(12) United States Patent
Bijelic et al.

(10) Patent No.: US 11,590,339 B2
(45) Date of Patent: Feb. 28, 2023

(54) DEVICE AND METHOD FOR CONTROLLED AND MONITORED TRANSDERMAL DELIVERY OF ACTIVE AGENTS AND USE THEREOF

(71) Applicant: FUNDACIÓN TECNALIA RESEARCH & INNOVATION, Derio-Bizkaia (ES)

(72) Inventors: Goran Bijelic, Derio-Bizkaia (ES); Manuel Montejo Estevez, Derio-Bizkaia (ES); Matija Strbac, Derio-Bizkaia (ES)

(73) Assignee: FUNDACIÓN TECNALIA RESEARCH & INNOVATION, Derio-Bizkaia (ES)

( * ) Notice: Subject to any disclaimer, the term of this patent is extended or adjusted under 35 U.S.C. 154(b) by 505 days.

(21) Appl. No.: 16/625,141

(22) PCT Filed: Jun. 23, 2018

(86) PCT No.: PCT/EP2018/066839
§ 371 (c)(1),
(2) Date: Dec. 20, 2019

(87) PCT Pub. No.: WO2019/002154
PCT Pub. Date: Jan. 3, 2019

(65) Prior Publication Data
US 2021/0290942 A1 Sep. 23, 2021

(30) Foreign Application Priority Data
Jun. 28, 2017 (EP) .................................... 17382407

(51) Int. Cl.
*A61N 1/04* (2006.01)
*A61N 1/36* (2006.01)
(Continued)

(52) U.S. Cl.
CPC .......... *A61N 1/0448* (2013.01); *A61K 9/0009* (2013.01); *A61N 1/325* (2013.01); *A61N 1/326* (2013.01); *A61N 1/36034* (2017.08)

(58) Field of Classification Search
CPC ...... A61N 1/0448; A61N 1/325; A61N 1/326; A61N 1/36034; A61K 9/0009; A61K 9/7069; A61K 9/7053; A61K 9/7084
See application file for complete search history.

(56) References Cited

U.S. PATENT DOCUMENTS 6,546,282 B1   4/2003  Inoue et al.
6,678,554 B1 * 1/2004  Sun ........................ A61N 1/044
                                                         604/20
(Continued)

FOREIGN PATENT DOCUMENTS

DE   102010024558 A1 * 12/2011 ............. A61N 1/044
DE   102010024558 A1    12/2011
(Continued)

OTHER PUBLICATIONS

International Search Report dated Sep. 25, 2018 re: Application No. PCT/EP2018/066839, pp. 1-6, citing: WO 90/62857 A1, DE 10 2010 024558 A1, WO 2008/038241 A2, WO 2006/133103 A2 and US 2011/0230857 A1.

(Continued)

*Primary Examiner* — Mallika D Fairchild
(74) *Attorney, Agent, or Firm* — Cantor Colburn LLP

(57) ABSTRACT

An iontophoretic patch for transdermal delivery of biologically active agents includes at least two electrodes in contact with at least two hydrogel reservoirs. At least one of the hydrogel reservoirs carries at least one active agent and, in use of the iontophoretic patch, is disposed on a user's skin and delivers at least one active agent into the skin. The patch includes a control unit to generate a stimulation pattern having stimulation parameters delivered to stimuli locations (Continued)

on the skin. A stimulation unit generates a time sequence of pulses from the stimulation parameters generated by the control unit. The patch further includes a demultiplexing unit configured to perform independent spatio-temporal distribution of the electrical pulses in the time sequence of pulses to at least one electrode; at least one optical sensing system, for continuously measuring an amount of the active agent in the hydrogel reservoir; and a feedback unit.

17 Claims, 12 Drawing Sheets

(51) Int. Cl.
    *A61K 9/00*     (2006.01)
    *A61N 1/32*     (2006.01)

(56) References Cited

U.S. PATENT DOCUMENTS

| | | |
|---|---|---|
| 8,428,709 B1 | 4/2013 | White et al. |
| 9,327,105 B2 | 5/2016 | Ramdas et al. |
| 2001/0009983 A1 | 7/2001 | Walter et al. |
| 2004/0193089 A1 | 9/2004 | Fischer et al. |
| 2006/0110292 A1* | 5/2006 | Deverse ............... G01F 23/292 422/68.1 |
| 2007/0021711 A1 | 1/2007 | Matsumura et al. |
| 2009/0118710 A1 | 5/2009 | Kortzeborn |
| 2011/0009805 A1* | 1/2011 | Imran ............... A61N 1/0428 604/20 |
| 2011/0230857 A1 | 9/2011 | Herbst |
| 2015/0369795 A1* | 12/2015 | Tsow ............... G01N 33/497 73/23.3 |
| 2016/0279434 A1 | 9/2016 | Edwards |

FOREIGN PATENT DOCUMENTS

| | | |
|---|---|---|
| EP | 0616545 A1 | 9/1994 |
| EP | 0830175 A1 | 3/1998 |
| EP | 1067985 A1 | 1/2001 |
| EP | 2949359 A1 | 12/2015 |
| EP | 2810688 B1 | 11/2016 |
| WO | 9952589 A1 | 10/1999 |
| WO | 0062857 A1 | 10/2000 |
| WO | 2006133103 A2 | 12/2006 |
| WO | 2008038241 A2 | 4/2008 |
| WO | 2008131072 A1 | 10/2008 |

OTHER PUBLICATIONS

Written Opinion dated Sep. 25, 2018 re: Application No. PCT/EP2018/066839, pp. 1-8, citing: WO 00/62857 A1, DE 10 2010 024558 A1 and WO 2008/038241 A2.

* cited by examiner

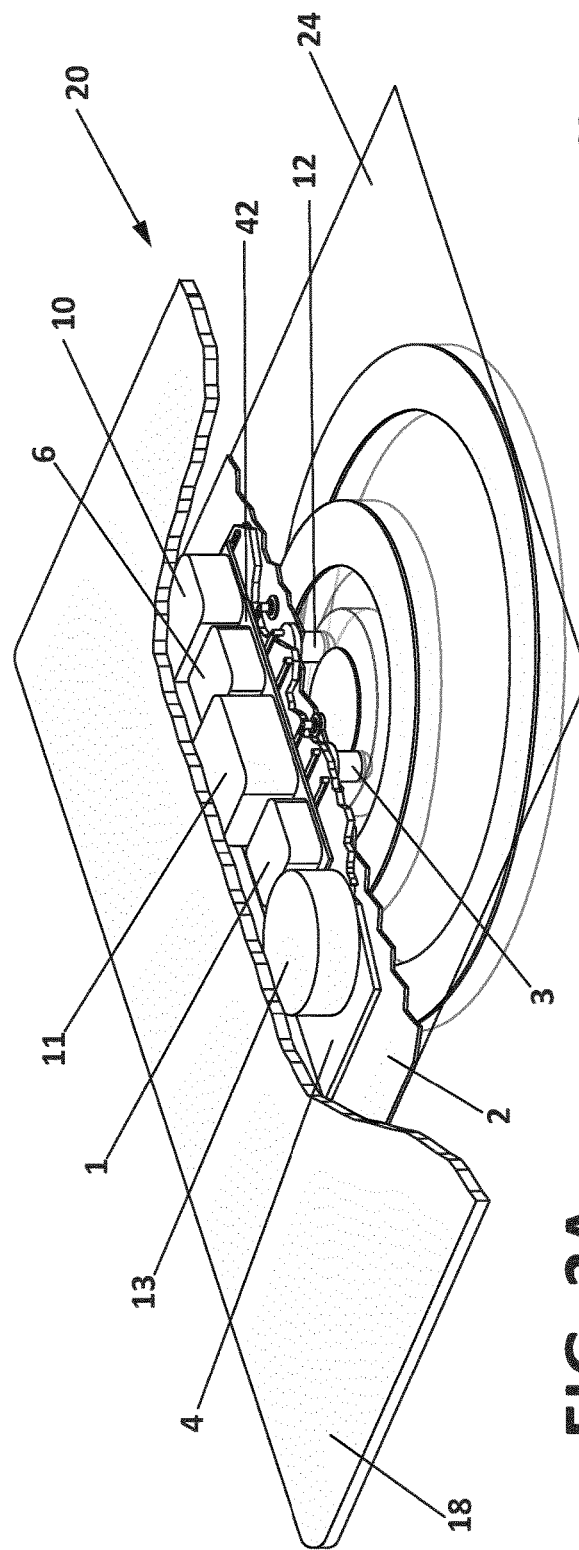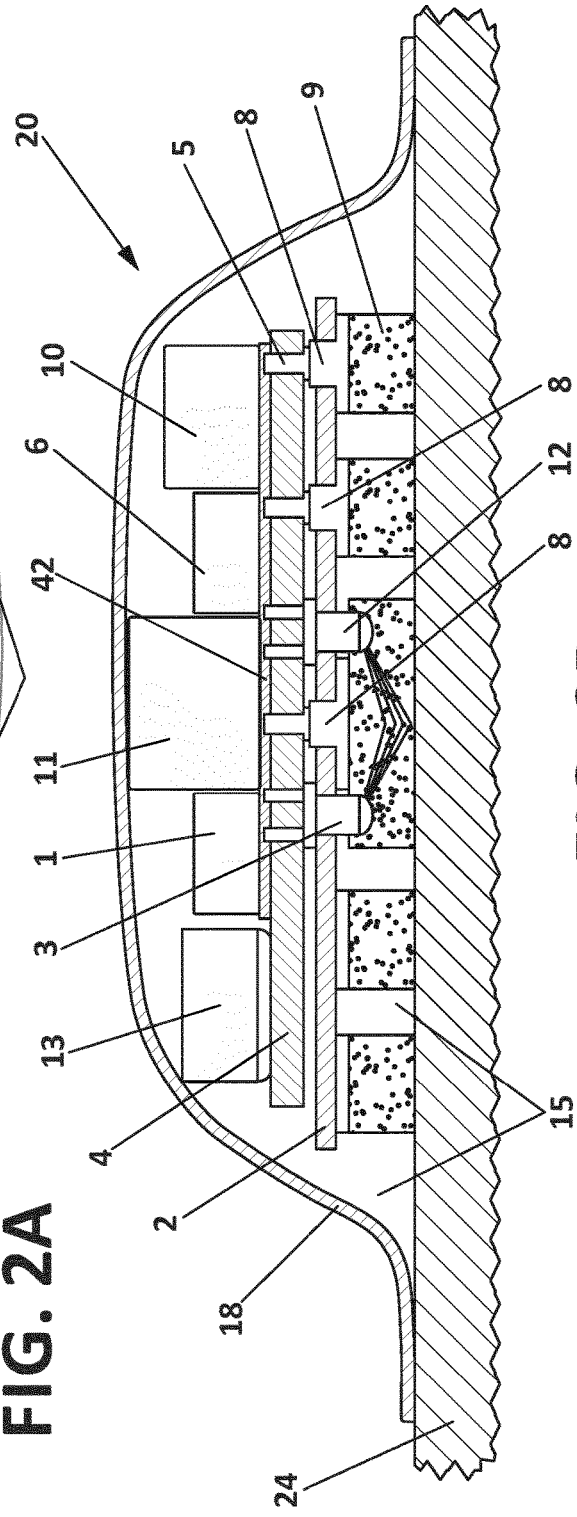
FIG. 2A
FIG. 2B

DEVICE AND METHOD FOR CONTROLLED AND MONITORED TRANSDERMAL DELIVERY OF ACTIVE AGENTS AND USE THEREOF

TECHNICAL FIELD

The present disclosure relates to controlled and monitored transdermal delivery of biologically active substances and agents, such as drugs, prodrugs, tissue growth factors, nanoparticles, biomedical probes such as biomarkers or allergen probes. More specifically, the present disclosure relates to products and methods for such transdermal delivery.

BACKGROUND

From wound healing to immuno-modulation and drug delivery, a large number of therapeutic strategies rely on the application of electric fields and currents to and through the skin with an electronic device comprising skin-contacting electrodes.

The main application of such devices is currently transdermal drug delivery, which represents an alternative to oral delivery of drugs and is poised to provide an alternative to hypodermic injection too. Currently the transdermal route has become one of the most successful and innovative focus in drug delivery, with around 40% of the drug candidates being under clinical evaluation related to transdermal or dermal systems. Transdermal delivery of drugs through the skin to the systemic circulation provides a convenient route of administration for a variety of clinical indications (Front Line Strategic Consulting Inc., 2002). The benefits of using transdermal drug delivery include improved systemic bioavailability resulting from bypassing the first metabolism. Variables due to oral administration, such as pH, the presence of food or enzymes and transit times can all be eliminated.

In the development of new transdermal drug delivery devices the object is most often to obtain controlled, predictable and reproducible release of drugs into the blood stream of the patient. The transdermal device acts as a drug reservoir and controls the rate of drug transfer. When the transdermal flux is controlled by the device instead of skin, delivery of the drug is more reproducible leading to smaller inter and intra subject variations, since the drug release from the device can be controlled more accurately than the permeability of the skin (Guy et al., 1992).

One of the possible techniques used for transdermal delivery is called iontophoresis. It is the application of an electric potential that maintains a constant electric current across the skin and enhances the delivery of ionized as well as unionized moieties (Williams et al., 1992). The ion movement in the skin and in a hydrogel is governed by the combined influence of the ionic concentration gradient and the electric field, as defined by the Nernst-Planck equation. When a direct electric current activates the planar electrodes of an electrode array placed over a piece of skin, anions— ions with a negative charge—are repelled from the negative electrode. Cations—positively charged ions—are similarly repelled from the positive electrode. Because of the shape of the electric field generated by the planar electrodes, ionic movement forms an electric current driven through the skin in the direction of the electric potential gradient. The net effect of iontophoresis becomes evident whenever the movement of the ions due to the electric field is dominant over passive diffusion of ions through the skin. The higher the current density and the amount of time the electric current flows through the skin, the larger the quantity of ions that penetrate into the skin. Iontophoresis is capable of expanding the range of compounds that can be delivered transdermally. Along with the benefits of bypassing hepatic first pass effect, and higher patient compliance, the additional advantages that the iontophoretic technique offers can be summarized as follows (Williams et al., 1992, Williams et al., 1991 and Glikfeld et al., 1988): delivery of both ionized and unionized drugs; depending on the current applied it is enabling continuous or pulsatile delivery of drug; permitting easier termination of drug delivery; offering better control over the amount of drug delivered since the amount of compound delivered depends on applied current, duration of applied current, and area of skin exposed to the current; restoration/preservation of the skin barrier functions without producing severe skin irritation; improving the delivery of polar molecules as well as high molecular weight compounds; ability to be used for systemic delivery or local (topical) delivery of drugs; reducing considerably inter and/or intra subject variability in view of the fact that the rate of drug delivery is more dependent on applied current than on stratum corneum characteristics.

The control of the dosage of drug delivered into the body is a critical issue for many medical applications. Some solutions, such as the ones provided by US2001009983 (A1) and U.S. Pat. No. 9,327,105 (B2), have been proposed to release a predefined current profile achieving this way a limited control on the drug delivered.

In order to overcome such limitation, other disclosures as an example U.S. Pat. No. 8,428,709 (B1), EP2949359 (A1), EP2810688 (B1), WO2008131072 (A1), US2007021711 (A1) and U.S. Pat. No. 6,546,282 (B1), provide a control system for the iontophoretic device based on the measurement of the current delivered by the device. The measured current value is used by the controller to adjust the current to a predefined delivering profile that matches the estimated drug delivered into the body. In an alternative proposal, EP0616545 (B1) measures the charge transferred to display the estimated cumulative amount of drug delivered into the body.

Another alternative approach to control how much drug is delivered into the body is provided, for example, in US2016279434 (A1), EP0830175 (B1) and US2009118710 (A1) where a controller modifies the release of drug depending on external parameters such as user age, skin type or environmental parameters such as local temperature and atmospheric pressure), or depending on the measurement of body parameters such as glucose concentration, or depending on the drug reservoir attached to the device.

Another alternative approach to control how drug is released into the body is provided by different designs of iontophoretic devices. As an example, US2004193089 (A1), uses a network of electrodes to achieve a spatial release of the drug. As another example EP1067985 (B1), measures impedance to control the electric field and hence how drug is delivered into the body.

Clearly, despite a great number of proposals in the field of iontophoresis-based devices, the control of the dosage, spatial and temporal delivery profile is based on measurements of current or voltage and consequent estimation of amounts of drug that is delivered. This approach has one major drawback, that is related to the fact that in all iontophoretic devices the current measured is reflecting the movement of all ions in the system and predominantly this current has origin in small mobile ions of the electrolyte solution and only a minor part of the current can be attributed to the movement and charge transfer of the drug molecules themselves. Having in mind the correlation between net current and the current that originally comes from charged drug molecules, a proportional relation may be established, but still dependent on many variable factors coupled with inter subject differences.

Hence, one of the current challenges is monitoring in real time the amount of drug that is delivered to the skin. Measuring this amount of drug on or in the skin directly involves a very complex methodology that is very difficult to integrate in a wearable or single use device.

SUMMARY

The disclosure provides an iontophoretic device for real time monitored and controlled transdermal delivery of biologically active substances and/or active agents, which overcomes the limitations of conventional devices and still comprises simple and cost/benefit efficient innovative solutions.

The present disclosure permits the direct drug concentration measurement and real time monitoring of localized delivery of active agent in confined elements/areas/volumes of the skin and underlying tissue, muscles, nerves or bones underlying the electrodes, providing also simultaneously a direct and real time drug concentration sensor-based regulation of the quantity of the active agent that is being delivered. The temporal regulation of a substance or biologically active agent release is especially important for instance in delivery of drugs to treat specific diseases where a concentration of the active agent should be maintained to a certain level. The localized delivery of a substance or biologically active agent in a certain area or volume is especially important when the substance or agent, for any reason, should not reach a specific part of the skin or user's body, in general.

The disclosure provides a patch which is capable of spatially and temporally controlling the transdermal delivery of an active agent in a confined part of the user's body, such as the skin and underlying tissue muscles, nerves or bones. At the same time, the patch is capable of monitoring and detecting the delivered amount of active substance and using this for active control of temporal and spatial delivery profile. The patch comprises integrated control means, for example based on a microprocessor. The patch may be autonomous and has integrated power supply means, for example in the form of a single use battery. Alternatively, the patch may require external power supply means.

According to a first aspect of the present disclosure, there is provided an iontophoretic device for transdermal delivery of biologically active agents comprising: at least two electrodes in contact with respective at least two hydrogel reservoirs, wherein at least one of said hydrogel reservoirs is configured to carry at least one active agent and, in use of the iontophoretic patch, to be disposed on a user's skin and deliver said at least one active agent into the user's skin; a control unit configured to generate a stimulation pattern comprising a plurality of stimulation parameters to be delivered to a plurality of electrical stimuli locations on the skin; a stimulation unit configured to generate a time sequence of pulses from said plurality of stimulation parameters generated by the control unit; a demultiplexing unit configured to, from the time sequence of pulses generated by said stimulation unit and from said stimuli locations generated by said control unit, perform independent spatio-temporal distribution of the electrical pulses comprised in said time sequence of pulses to at least one electrode of said at least two electrodes; at least one optical sensing system disposed in at least one of said hydrogel reservoirs, for continuously measuring an amount of said at least one active agent in said at least one hydrogel reservoir; a feedback unit configured to estimate an actual delivery profile of said at least one active agent from said measured amount of at least one biologically active agent; said control unit being further configured to continuously modify said stimulation pattern by changing at least one of said plurality of stimulation parameters to be provided to the stimulation unit and/or said stimuli locations to be provided to said demultiplexing unit.

In embodiments of the disclosure, the at least two electrodes are concentric, and said at least two hydrogel reservoirs with which said at least two electrodes are in contact, are also concentric.

In embodiments of the disclosure, the at least one optical sensing system comprises at least one light emitting means and at least one light detecting means.

In embodiments of the disclosure, the control unit is configured to control one or more of the following parameters of a stimulation pattern: polarity, amplitude, frequency of voltage/current pulses, duration of voltage/current pulses and activation of at least one electrode from the at least two electrodes.

In embodiments of the disclosure, a mixture of hydrogel and active agent comprised in said at least one hydrogel reservoir is translucent at the wavelength range of operation, thus enabling optical detection by said at least one optical sensing system.

In embodiments of the disclosure, the hydrogel comprised in said at least one hydrogel reservoir is configured to provide a tunable concentration gradient profile of active agent and tunable electrical conductivity, thus controlling concentration and electrical conductivity within the at least one hydrogel reservoir.

In embodiments of the disclosure, each electrode of said at least two electrodes comprises electrical contacts independent from electrical contacts of other electrodes of said at least two electrodes, thus enabling independent delivery of electrical stimuli.

In embodiments of the disclosure, the iontophoretic patch further comprising power supply means.

In embodiments of the disclosure, the at least one biologically active agent to be delivered in the skin is one of the following list: a drug, a prodrug, a tissue growth factor or a biomedical probe, said substance being in the form of a compound, protein, peptide, nucleotide, ribozyme, dsRNA, RNAi, vaccine or a combination thereof.

According to another aspect of the present disclosure, there is provided a use of the iontophoretic patch previously disclosed, in a treatment based on transdermal delivery of biologically active agents by iontophoretic techniques.

According to another aspect of the present disclosure, there is provided a use of the iontophoretic patch previously disclosed for the simultaneous delivery of a plurality of allergen probes in a method for diagnosing at least one allergy, the diagnostic method being based on transdermal delivery of biologically active substances by iontophoretic techniques.

According to another aspect of the present disclosure, there is provided a method of controlling the delivery of at least one active agent from a iontophoretic patch, comprising: delivering at least one active agent according to an initial profile by applying a stimulation pattern to at least two electrodes in contact with respective at least two hydrogel reservoirs, in contact with a user's skin, wherein at least one of said hydrogel reservoirs comprises said active agent, wherein said stimulation pattern comprises a plurality of stimulation parameters and electrical stimuli location; estimating the amount of said at least one active agent within said at least one hydrogel reservoir by measuring an optical parameter in said hydrogel reservoir; determining the actual delivery profile of active agent delivered to the skin by comparing the actual amount of delivered active agent with the amount thereof corresponding to said initial profile; if the actual delivery profile does not match the initial profile, modifying the stimulation parameters and/or stimulation location pattern to achieve the initial delivering profile. The steps of this method are repeated continuously to achieve the desired delivery profile.

Additional advantages and features of the disclosure will become apparent from the detail description that follows and will be particularly pointed out in the appended claims.

BRIEF DESCRIPTION OF THE DRAWINGS

To complete the description and in order to provide for a better understanding of the disclosure, a set of drawings is provided. Said drawings form an integral part of the description and illustrate an embodiment of the disclosure, which should not be interpreted as restricting the scope of the disclosure, but just as an example of how the disclosure can be carried out. The drawings comprise the following figures:

FIG. 2A shows a cross section of an iontophoretic patch according to an embodiment of the disclosure. FIG. 2B shows an outline representing the disposition of the electrodes and the electrode-skin interface layer.

DETAILED DESCRIPTION OF THE DRAWINGS

In this text, the term "comprises" and its derivations (such as "comprising", etc.) should not be understood in an excluding sense, that is, these terms should not be interpreted as excluding the possibility that what is described and defined may include further elements, steps, etc.

In the context of the present disclosure, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about" and "around" and "substantially".

The following description is not to be taken in a limiting sense but is given solely for the purpose of describing the broad principles of the disclosure. Next embodiments of the disclosure will be described by way of example, with reference to the above-mentioned drawings showing apparatuses and results according to the disclosure.

In the context of the present disclosure, the expression "biologically active substances" refers to drugs, prodrugs, tissue growth factors and biomedical probes, in the form of compounds, proteins, peptides, nucleotides, ribozymes, dsRNAs, RNAi, vaccines or any other form or any other substance which can be administered through the skin.

In the context of the present disclosure, the expressions "active agent", "bioactive agent" and "pharmaceutically active agent" may be used interchangeably to refer to an agent or substance that has measurable specified or selected physiologic activity when administered to a subject in a significant or effective amount or to a chemically, physically, or biologically active principle. It is to be understood that the term "drug" is expressly encompassed by the present definition as many drugs and prodrugs are known to have specific physiologic activities. As used herein, "prodrug" refers to a molecule that will convert into a drug. Prodrugs themselves can also be pharmacologically active, and therefore are also expressly included within the definition of an "active agent" as recited above.

The disclosure provides a device (a patch) which is capable of spatially and temporally controlling the transdermal delivery of a substance and/or the delivery of an active agent, such as a pharmaceutical molecule, in a confined part of the user's body, such as the skin and underlying tissue muscles, nerves or bones. Integrated control means are for example based on a microprocessor.

Figure 1A:
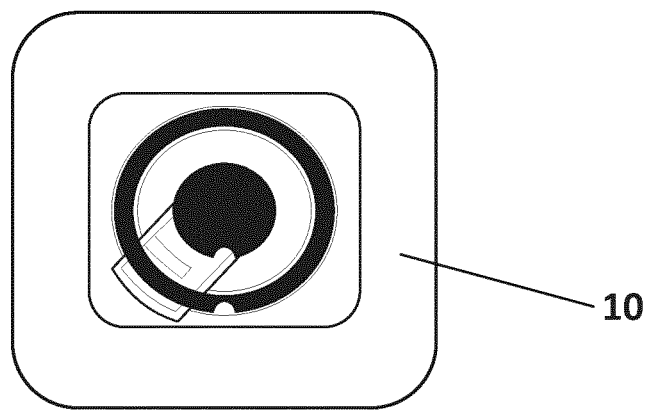
FIGS. 1A and 1B show respectively front and back views of an iontophoretic patch according to an embodiment of the disclosure.
Figure 1B:
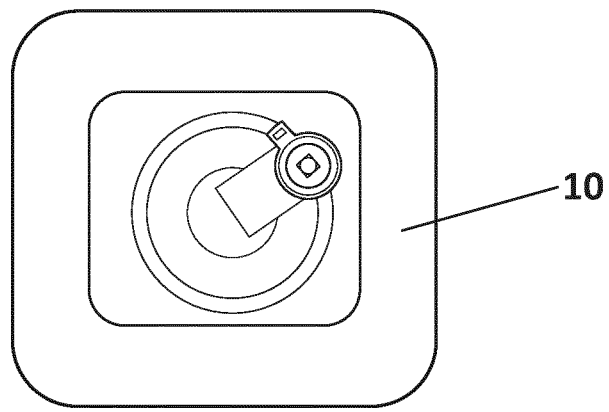
Figure 1C:
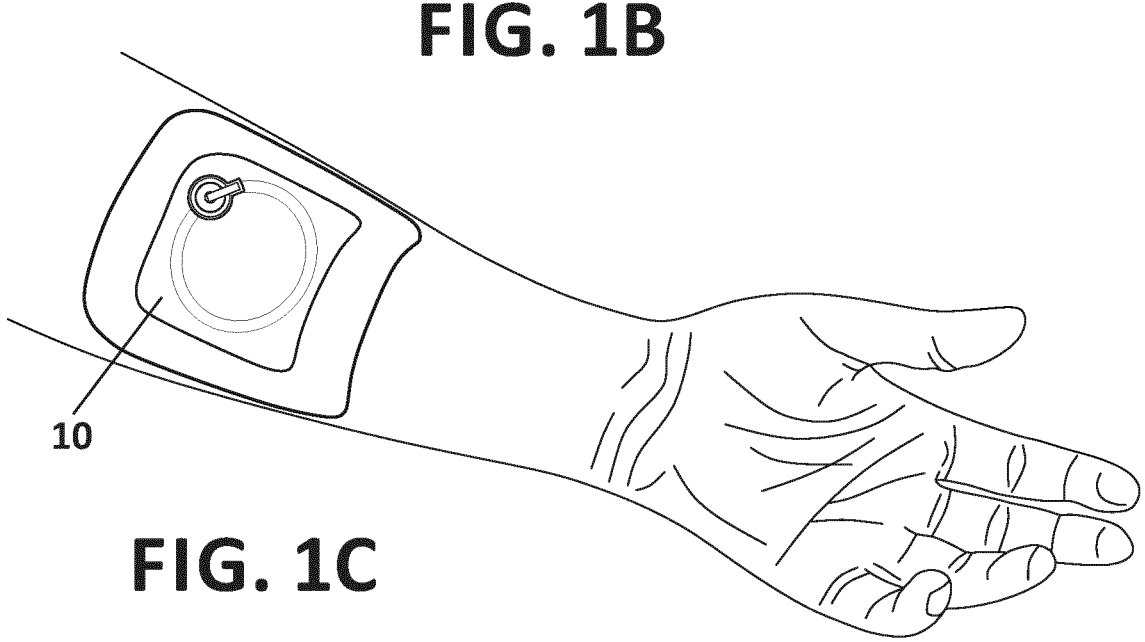
FIG. 1C illustrates the iontophoretic patch applied on the arm of a person.

FIGS. 1A and 1B show respectively front and back views of an iontophoretic patch 10 according to an embodiment of the disclosure. The patch can be disposable or rechargeable, both in terms of battery and in terms of additional dose of drugs/compounds. FIG. 1C illustrates a particular use of the patch 10, in this example applied on the arm of a person.

Figure 3A:
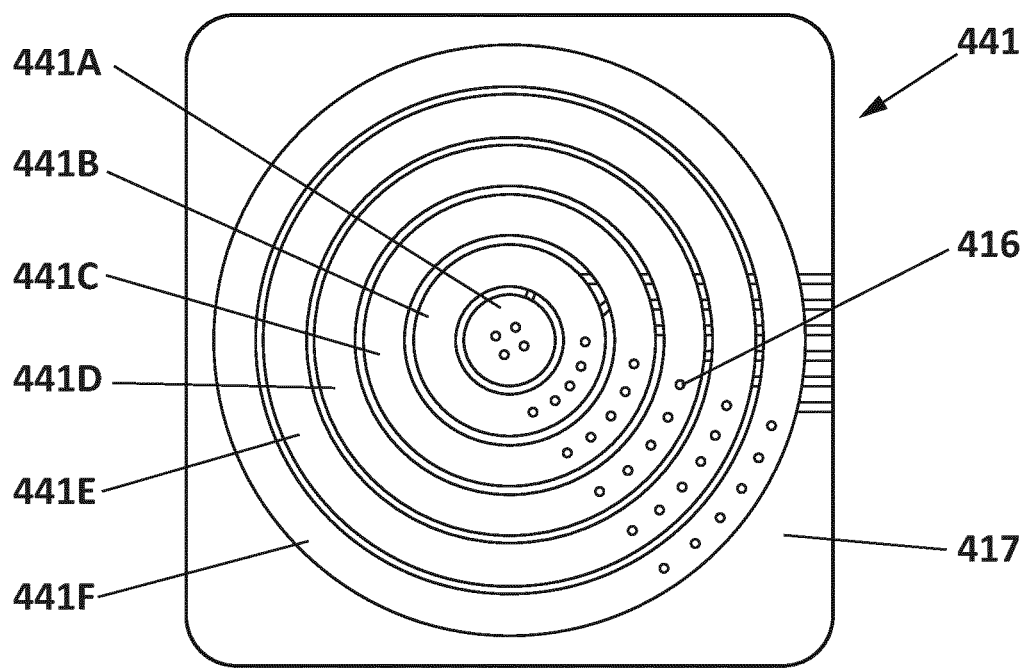
FIGS. 3A-3C show different representations of the electrode configuration in a patch according to different embodiments of the disclosure as examples.
Figure 3B:
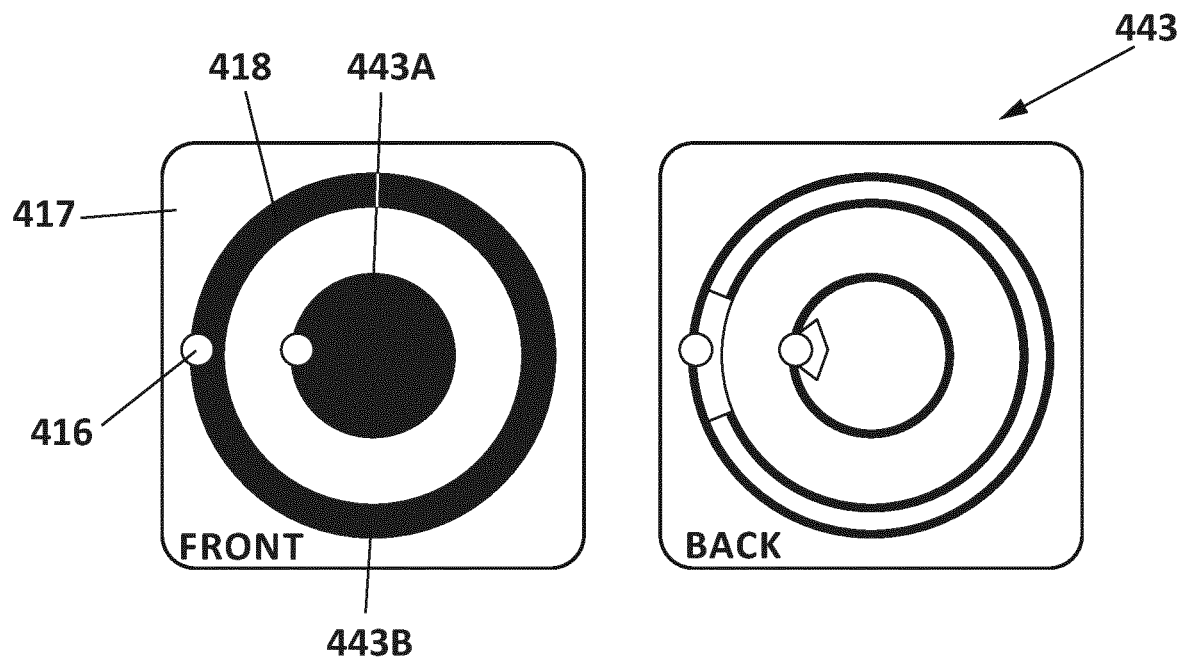
Figure 3C:
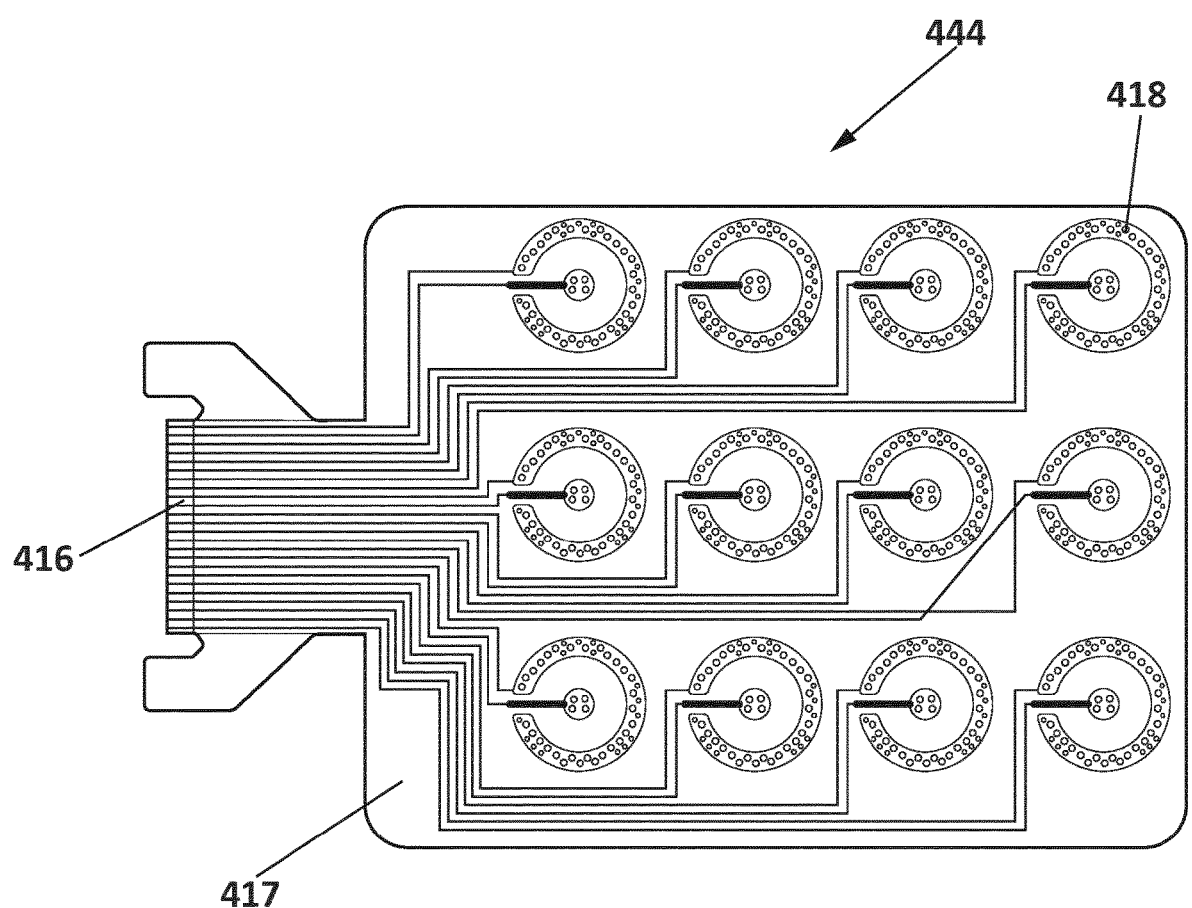

FIG. 2A shows a side view of an iontophoretic patch 20 according to an embodiment of the disclosure. In FIG. 2A, the outer layer or outer protection 18 has been partially removed for illustration purposes in order to show the inner part of the patch. For the same reason, a support or board 4 (comprising a dielectric substrate or layer, referred to as 4 in the figure, and at least one conductive zone 42) and an electrode substrate 2, comprised within the patch, have also been partially removed in order to show the electrodes 8 and associated drug reservoirs 9 comprised within the patch. FIG. 2B shows a cross-section of the iontophoretic patch 20 of FIG. 2A. In use, the patch 20 is disposed on the skin 24 of a user. The general mode of operation of the patch 20 is as follows: electronic discharge means (a block diagram of which is explained in detail with reference to FIG. 4) comprised, embedded or disposed within patch 20 is responsible for generating a stimulation pattern formed by electrical stimulation parameters and electrode activation configuration and for activating electrodes 8 according to the stimulation pattern. Electronic discharge means comprises, among other elements, at least one electrode set or electrode array 8. The at least one electrode set or electrode array 8 comprises a plurality of electrodes. There are at least two electrodes 8. In the embodiment shown in FIGS. 2A and 2B, three concentric electrodes 8 have been used. In other words, there is a first electrode having a certain shape, a second electrode which at least partially surrounds the first electrode and a third electrode which at least partially surrounds the second electrode. In the shown embodiment the shape of the inner electrode is round or oval, but it can have any other shape. Some shapes are more convenient than other ones for the external electrodes: the most convenient ones are circular, oval or of a polygon having soft angles, such as more than eight angles. In FIGS. 2A and 2B the surrounding electrodes are formed by a ring-shaped strip. The width of the electrodes and the distance between adjacent ones can vary, depending on the specific application for which the patch is designed. Other implementations of the at least two electrodes 8 may be embodied. FIGS. 3A-3C show different electrode configurations that may be embodied in a patch.

The electrodes 8 are assembled, embedded or attached to the electrode substrate 2. The electrode substrate 2 can be made of polyester, polycarbonate, silicon rubber, or any other thin flexible material which can be knitted into textile or processed as thin foil or laminated structure or any other manufacturing technique for producing a thin layer. At their opposite side with respect to the electrode substrate 2, the electrodes 8 are disposed on or attached to a hydrogel reservoir 9 (also referred to as drug reservoir) from which an active agent may be delivered into the user's skin 24. In the embodiment shown in FIGS. 2A and 2B the hydrogel reservoir 9 is implemented following the same shape and disposition of the electrodes, that is to say, by means of three concentric ring-shaped reservoirs 9 onto which the three electrodes 8 are respectively disposed. The space between concentric reservoirs 9 is filled with an insulating material or medium 15, such as air. There may be one hydrogel reservoir 9 per electrode 8.

The hydrogel reservoir 9, which holds the active substance to be applied into the user's skin when the patch is used to deliver an active substance into the user's skin, can be implemented as a coating matrix. The material which forms this matrix or reservoir 9 is a hydrogel. The substance can be dissolved in a solvent and/or dispersed in a polymer, with or without excipients, and this mixture then generates the matrix by solvent evaporation and/or gelification and/or any other polymerization processes. Alternatively the hydrogel reservoir 9 can be formed as gel pad to which the active substance is introduced through incubation, dispensing, spraying or injection process. The material must be suitable for use as a reservoir for a substance or drug solution, such as an ionic drug solution, in its normal condition, or suitable therefore when a suitable hydrophilic additive is loaded or applied to the material.

The matrix or reservoir 9 should adhere to the electrode and maintain intimate mechanical and electrical contact with both electrode and skin, either by using an adhesive hydrogel or by adding an adhesive to the reservoir, as already mentioned. The matrix must contain and retain significant amount of water or other solvent and dissolved substances to diffuse within the internal matrix structure and reach the skin surface. The matrix must not allow the solvent or soluble substances to leak in bulks. Non-limiting examples of materials which provide these properties are: methacrylate based hydrogel polymers or other polymers such as PVA, PEO, PEG, PVP, CMC and their mixtures or other conventional polymers and their mixtures, where processes of polymerization, processing with porogen substances and cross linking of the polymers are used to tailor their properties. Other materials, such as textiles, foams or sintered mineral materials can also be used, provided they meet the requirements already described. Leaking of the active substance from the matrix is prevented thanks to the physical and chemical matrix properties, such as the hydrophilic nature of the matrix material and its internal structure, such as the matrix network pore size, hydrogel polymer cross linking grade, and so on.

The hydrogel reservoir 9 may comprise, contain or hold at least one active agent to be transdermally delivered into the skin 24. Non-limiting examples of biologically active agents which can be held in the hydrogel reservoir 9 are drugs, prodrugs, tissue growth factors and biomedical probes, in the form of compounds, proteins, peptides, nucleotides, ribozymes, dsRNAs, RNAi, vaccines or any other form or any other substance which can be administered through the skin. The substances to be delivered are out of the scope of this disclosure.

Different types of biocompatible hydrogel can be used, be they synthetic or natural, be they physically crosslinked or chemically crosslinked, etc. The hydrogel may be or may comprise a polymer. Such polymers include, but are not limited to, the following examples and blends thereof: polyethylene glycol and derivatives, polyvinyl pyrrolidone, polyvinyl alcohol, chitosan and derivatives, acrylic acid and derivatives, hydrogels prepared by click chemistry (example: thiol-ene reaction), alginate and derivatives, silk fibroin and derivatives, etc. The hydrogel may be homogeneous in composition or alternatively be comprised of at least two joined subsets of a different chemical nature. It may also exhibit isotropic or anisotropic properties. The patch can be disposable or rechargeable, meaning for example that an additional dose of drugs/compounds is recharged when required. In this case, the process of reusing the patch is for example done by replacing the used hydrogel (or other drug carrying matrix) reservoir 9 with a new hydrogel reservoir loaded with active substance, through a strip off & replace procedure.

The hydrogel reservoir 9 may be conductive and adhesive to the skin 24. In this case no additional adhesive element is required. Alternatively, a different type of hydrogel may be used which does not provide sufficient adhesion to the skin for the patch to fulfill its intended function, in which case an additional contact-enforcing element is needed. This element may be an adhesive component integrated into the patch, or alternatively an adequate device (for example, an elastic strap) that mechanically maintains the patch in intimate contact with the skin.

The hydrogel may be configured to provide tunable concentration gradient profile of active agent and tunable electrical conductivity. This means that the hydrogel has the ability to control and achieve any desirable concentration and distribution of the active agent in the reservoir 9 as well as any desirable electrical conductivity of the reservoir 9. In this context, desirable concentration, distribution or electrical conductivity refers to well-known concentrations, distributions or electrical conductivities as disclosed in prior art patches. The term tunable refers to said ability to control and achieve the desirable values of concentration, distribution or electrical conductivity.

Electronic discharge means also comprises a stimulation unit 6, a demultiplexing unit 10, a control unit 11 and a feedback unit 1. The components comprised in the electronic discharge means are supported or embedded on board or support 4, such as, but not limiting, a PCB (printed circuit board). Typical boards 4 comprise a dielectric substrate layer (made of, for example, of a plastic material, and identified in FIG. 2B with reference 4) and a conductive layer or zone 42 that enables electric contact with the components disposed on the dielectric substrate of board 4. The stimulation unit 6, demultiplexing unit 10, control unit 11 and feedback unit 1 are disposed or embedded on the dielectric substrate of the board 4. These components may be physically comprised in a single chip or in several ones. In the implementation shown in FIGS. 2A and 2B, each component 6, 10, 11, 1 has been implemented in a different chip.

Electric contacts (also referred to as leads or wires) 5 connected to the electrodes 8 are in electrical contact with the conductive layer or zone 42 of the board 4, thus enabling electric communication between the electrodes 8 and the demultiplexing unit 10 attached to board 4, as will be described with reference to FIG. 4. The electrodes 8 may be thin-film electrodes, although any other type of suitable electrodes may be used instead. The electrodes 8 are configured to be activated/deactivated and to apply stimulation parameters following a stimulation pattern applied on the user's skin 24.

Electronic discharge means also comprises an optical sensing system 3, 12 for directly measuring the drug concentration in the hydrogel reservoir(s) 9 and therefore for monitoring at least the temporal delivery of active agent in confined elements/areas/volumes of the skin 24 and underlying tissue, muscles, nerves or bones, underlying the electrodes 8. This monitoring of at least temporal delivery of active agent is done as follows: The optical sensing system 3, 12 measures the amount of remaining active agent within a hydrogel reservoir 9 along time. This means that the non-remaining amount of active agent (with respect to the well-known, total amount of active agent originally present in the hydrogel reservoir 9) within the hydrogel reservoir 9 has already been delivered into the skin. Consecutive measurements of the concentration of active agent in the reservoir 9 are taken to determine the delivered amount of active agent to the skin. Measurements are done in predefined time intervals, such as, but not limiting, at sampling frequencies from 0.1 to 100 Hz. From the measurements obtained by the optical sensing system 3, 12, the feedback unit 1 calculates a temporal profile of delivery of active agent to the skin. In other words, a light signal measured by the optical sensing means is transferred to (translated into) a concentration value throughout the delivery session performed by the patch. From the information obtained by the feedback unit 1 and provided to the control unit 11, the control unit 11 decides which electrical stimuli and which electrodes must be activated next, thus controlling the electric field inside the skin and therefore controlling the delivery of active agent within the skin. This is done at certain time intervals, such as, but not limiting, at sampling frequencies from 0.1 to 100 Hz. Thus, real time control (that is to say, temporal control or control in time axis) of the quantity of the active agent that is being delivered into the skin 24 is achieved by means of this optical sensing system 3, 12. The optical sensing system 3, 12 may comprise a plurality of optical sensing elements. In this case, the optical sensing system 3, 12 measures the drug concentration in different locations of a hydrogel reservoir 9. Therefore, this enables the monitoring of the spatio-temporal delivery of active agent in confined elements/areas/volumes of the skin 24 and underlying tissue, muscles, nerves or bones, underlying the electrodes 8. From the measurements obtained by the plurality of elements included in the optical sensing system 3, 12, the feedback unit 1 calculates a spatio-temporal profile of delivery of active agent to the skin. And then, the control unit 11 decides which electrical stimuli and which electrodes must be activated next. The electric contacts 5 are made of a conductive material. Non-limiting examples of conductive materials are copper, silver, gold, carbon or any other conductive material or combination thereof. Each contact 5 can be activated independently through demultiplexing unit 10, as shown for example in FIG. 2B and in FIGS. 3A-3C and explained in view of FIG. 4. The desired stimulation pattern can be delivered to at least two electrical contacts 5. The electrical contacts 5 can be manufactured by means of conventional manufacturing techniques, such as screen printing, PVD or CVD deposition on the corresponding side of the electrode substrate 2. For example, miniature holes in the electrode substrate 2 may be filled with a conductive material, thus establishing an electrical connection (via connection) between the electrodes 8 and the contacts 5.

The patch 20 may be autonomous and may have integrated power supply means (DC power supply means) 13, for example in the form of a battery 13, such as a single use battery. In the illustrated patch 20, the power supply means 13 is comprised within the volume delimited by the outer protection 18. When a single-use battery is used, the patch 20 is disposable. Non-limiting examples of batteries are button batteries or flexible-film batteries. In FIGS. 2A and 2B, the power supply means 13 is disposed on board 4. Alternatively, the patch may require external power supply means. The patch 20 may further comprise a light-emitting indicator (not shown in FIGS. 2A-2B), configured to emit light when the patch 20 is in ON state (working) and not to emit light when the patch 20 is in OFF state. In a non-limiting example the light-emitting indicator is a LED (light emitting diode).

The device (patch) 20 comprises an outer protection or protective element 18 that protects and insulates the electronic circuitry and maintains the mechanical integrity of the patch. The part or side of the protective element 18 designed to be in contact with the user's skin 24 may be coated with an adhesive, thus ensuring the position and intimate contact of the patch 20 with the subject's skin 24. This is of particular interest when the hydrogel reservoir 9 is not adhesive enough to ensure positioning and integrity of the patch/skin interface. When the hydrogel reservoir 9 is adhesive enough, the protective element 18 may be used only for insulation and protection of the electronic circuitry housed within the patch from the environment. The protective element 18 may be made of a flexible, electrically insulating, porous material. Non-limiting examples of such materials are polyurethane foam processed in thin film, polyester, nylon or cellulose, polymer reinforced cellulose or any other suitable conventional material.

The electronic discharge means of patch 20 is capable of monitoring and detecting the delivered amount of active agent and uses this detected amount for active agent to control the temporal and spatial delivery profile. FIG. 4 shows a functional diagram of the electronic discharge block 40 of the patch 20. In the shown diagram, the electronic discharge block 40 is composed of the main elements already disclosed with reference to FIGS. 2A and 2B: electrodes 8, hydrogel reservoir 9 (typically one per electrode, although in FIG. 4 it is diagrammatically represented as a single block 9), optical sensing system(s) 3, 12, feedback unit 1, control unit 11, stimulation unit 6 and demultiplexing unit 10. The electronic discharge means enables delivery of electrical stimuli either in voltage or in current control mode.

The input power (current or voltage) to be sent to each electrode 8 is individually modulated and converted into the required/programmed energy pulses or electrical stimuli (stimulation pattern), which will be received by the electrodes 8. This is done by control unit 11, which comprises processing means, such as, but not limiting, a programmable microprocessor, which controls the stimulation unit 6 and the demultiplexing unit 10. The substance kept within the hydrogel reservoir(s) 9 is then delivered to the skin 24. The control unit 11 handles the different transdermal drug delivery conditions. Its processing means is provided with programmable software configured for controlling the intensity, sequence, frequency, rate, timing information, location of the delivered stimuli and electrode polarity and any other parameter supplied for managing the substance delivery. This is achieved by varying the electric current or voltage applied to the electrodes 8 (current or voltage which is applied to one or more electrodes individually, that is to say, the current or voltage to be applied to one electrode is independent from the current or voltage to be applied to any other electrode). The control unit 11 can be programmed to provide a variety of substance delivery profiles. The duration and frequency of the delivery varies based upon the treatment protocol (medical prescription).

Figure 4:
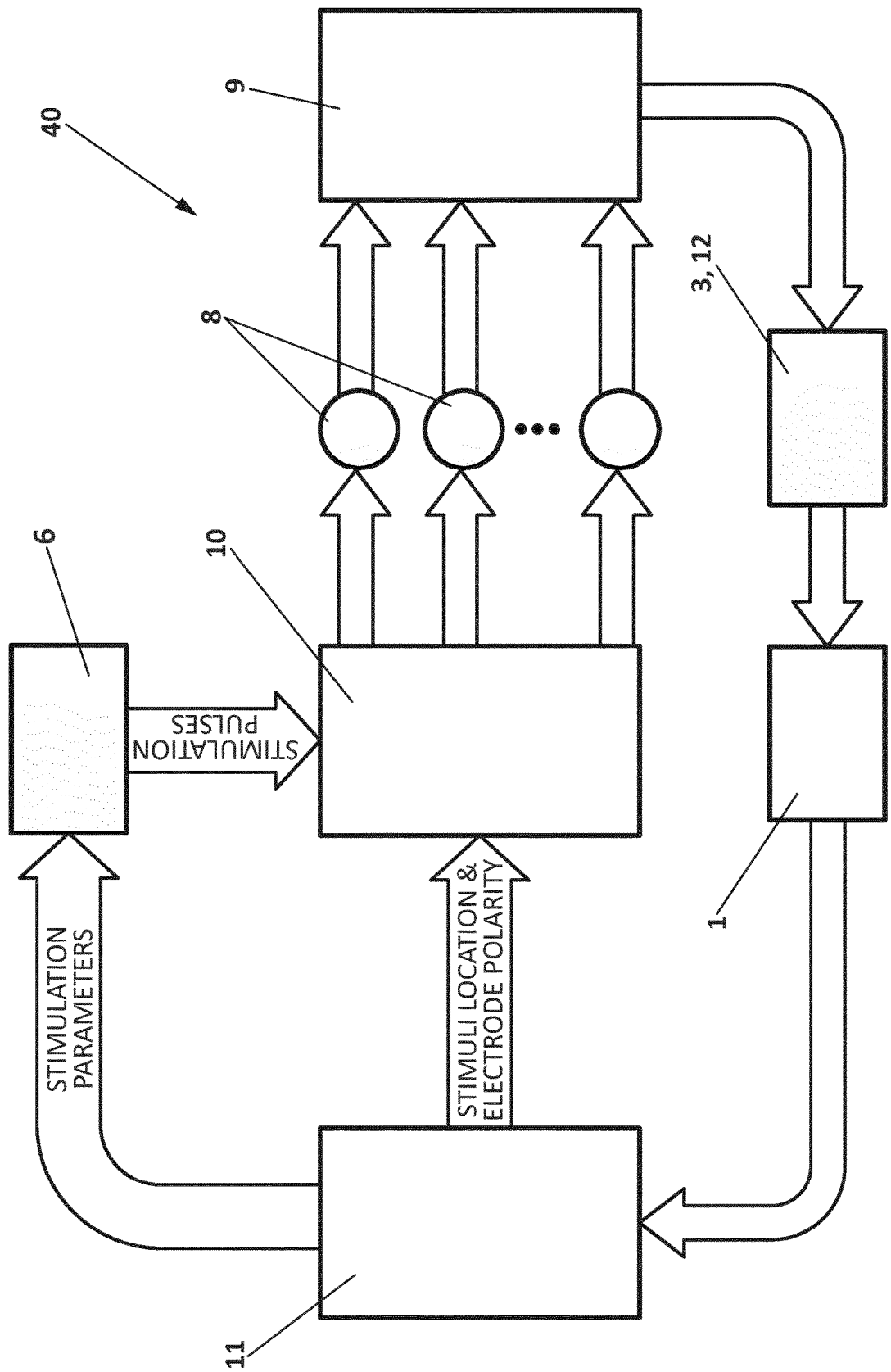
FIG. 4 shows a functional diagram of the functional elements of the patch according to an embodiment of the disclosure, as well as the relationship between said functional elements.

The general working of the patch 20 (in particular, of its electronic discharge means 40) is shown in the functional diagram of FIG. 4. Stimulation unit 6 generates current or voltage controlled stimulation pulses in the form of a pulsed waveform or plet (time sequence of a plurality of pulses of same or different frequency and/or amplitude). In order for the stimulation unit 6 to generate the sequence of pulses, the stimulation unit 6 preferably comprises a single channel voltage and/or current generator, configured to generate a plet from stimulation parameters generated by the control unit 11. The stimulation parameters of the plet are determined by the control unit 11. The stimulation parameters of the pulsed waveform are some or all of the following parameters: stimulation amplitude, DC, AC, frequency, pulse duration, duration of absence of pulse or pulsed stimuli, where the delivered pulses can n be mono-phase, bi-phase, bi-phase compensated or any other conventional pulsed stimuli. Each pulse in the plet can be distributed or assigned to one or more electrodes 8. This assignation is executed by the demultiplexing unit 10 following the instructions of the control unit 11, which indicates to the demultiplexing unit 10 the stimuli location (selection of the electrode(s) to which each pulse is to be delivered) and polarity of the pulse delivered to the electrode(s). In other words, the adequate combination of active electrodes to be stimulated with the pulses generated by the stimulation unit 6, is dictated by the control unit 11. This adequate combination of active electrodes is executed by demultiplexing unit 10. The release of active agent, including its amount and penetration depth, from the hydrogel reservoir 9 is thus controlled by the control unit 11 through the sequence of electrode activation following the pulse distribution (plet) performed by the demultiplexing unit 10. In sum, the stimulation unit 6 generates a time sequence of a plurality of pulses according to the parameters selected/calculated by the control unit 11, which additionally selects/calculates to which electrode or electrodes and with which polarity each pulse must be applied. The control unit 11 comprises means for independently controlling the different electrical stimuli parameters for each electrode, such as polarity, duration, amplitude, frequency or any other parameter that an expert can contemplate. At any instant in time when stimuli are applied, at least one electrode serves as an anode and at least one electrode serve as a cathode. The polarity of the electrodes can be changed by the control unit 11 at any time instant when stimuli are applied. Besides, any electrical stimuli parameter delivered to two or more electrodes can be constant or variable (changed in time). This is all achieved by a programmable circuit, such as a microcontroller, comprised in control unit 11, which comprises control means having stimulation programs, the execution of which can be either predefined or based on a closed-loop control system algorithm relying on biofeedback sensor signals. The stimulation program can be customized for each active substance and matrix and for each specific application. The control unit 11 also performs internal calibration prior to stimulation, where dosage control is adaptable for various targeted drugs and formulations including encapsulation or other carrier particles. The electrical stimulation parameters are delivered to the desired electrode configuration in a time-dependent predefined protocol. The programmable circuit, such as microcontroller, is also programmed to control the energy consumption from the power source.

As already said, the amount of active agent in the hydrogel reservoir 9 is measured by the optical sensing system 3, 12. Consecutive measurements of the concentration of active agent in the reservoir 9 are taken to determine the delivered amount of active agent to the skin. Measurements are done in predefined time intervals, such as, but not limiting, at sampling frequencies from 0.1 to 100 Hz. Based on the measured data, feedback unit 1 determines or estimates the actual active agent delivery profile. This may be done as follows: The original concentration (t=t0) of active agent within the hydrogel reservoir 9 is known and stored, for example in memory means associated to a microprocessor. The concentration of active agent in the hydrogel reservoir is measured (t=t1). The amount of released active agent is the difference between the well-known original concentration (t=t0) and the measured concentration at t=t1. The value to the amount of released active agent is stored (for example in memory means associated to a microprocessor). This process is repeated continuously, in such a way that a series of temporal data points represents how the active agent is being delivered in the skin along time. Control unit 11 compares the estimated delivery profile provided by the feedback unit 1 with a desired delivery profile, for example a delivery profile established according to medical prescription. Based on the result of this comparison, the control unit 11 updates the stimulation pattern by changing the stimulation parameters (through the stimulation unit 6) and/or the stimulation location and/or polarity (through the demultiplexing unit 10).

Figure 5:
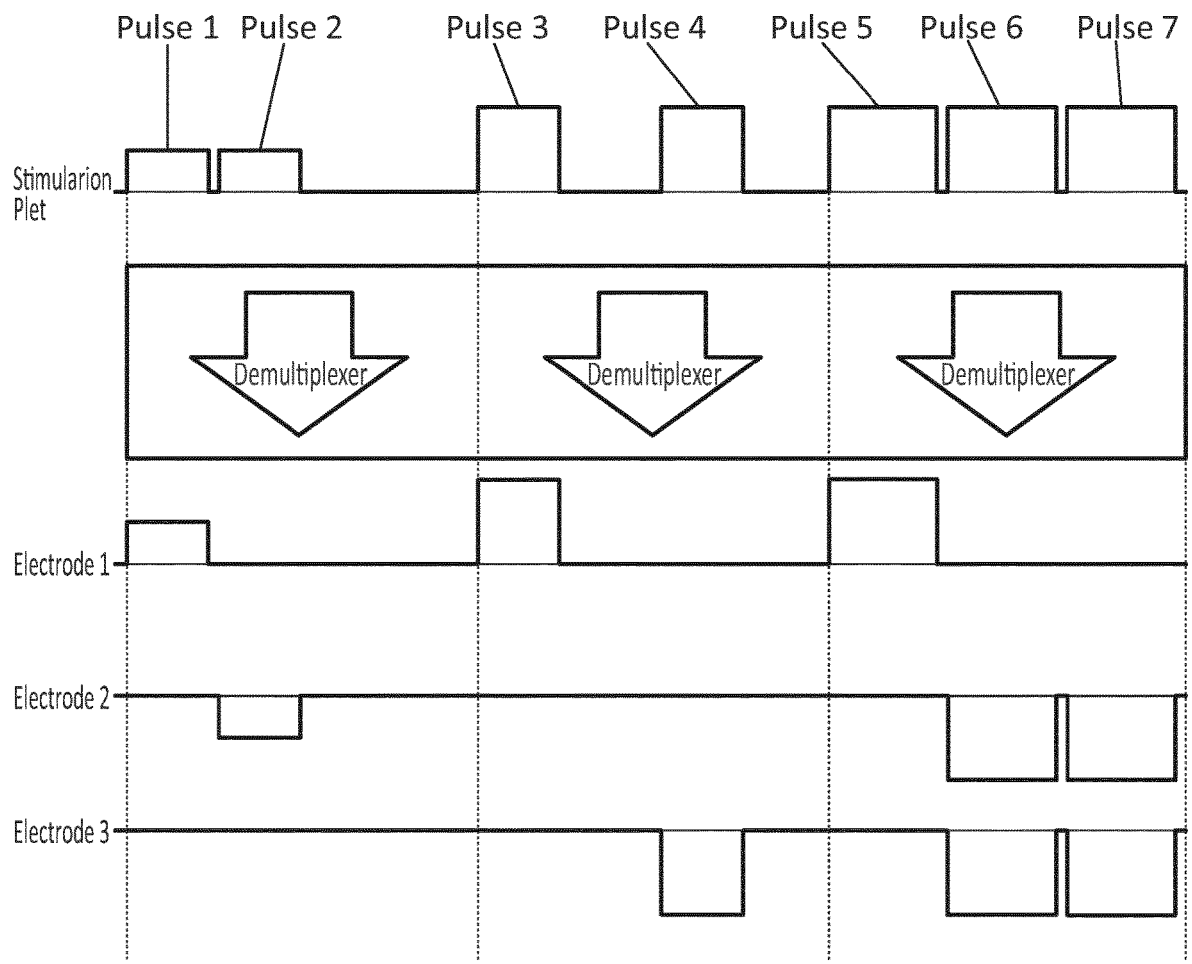
FIG. 5 illustrates the generation, multiplexing and delivery of pulsed signals to be applied to an electrode, and consequent spatio/temporal drug delivery profiles, in accordance with embodiments of the disclosure.
Figure 5:
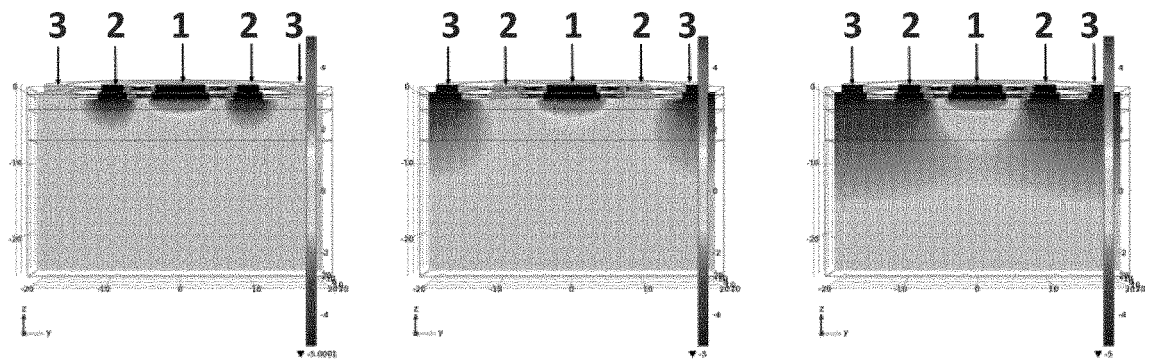

FIG. 5 shows an example of a pulsed waveform (stimulation plet) that may be applied to an electrode array in accordance with embodiments of the disclosure. The pulsed waveform or plet is defined by its parameters, such as pulse amplitude, pulse frequency, pulse duration, duration of absence of pulse, etc. This pulsed waveform is generated by stimulation unit 6 following the instructions of the control unit 11 and is provided to the demultiplexing unit 10 which sends, at every time instant, each pulse of the pulsed waveform to one or more electrodes of the electrode array 8 (in FIG. 5, referred to as electrode_1, electrode_2 and electrode_3) according to the instructions provided by the control unit 11 in terms of location (electrode selection) and polarity. For example, the first pulse of the pulsed waveform is applied to electrode_1, the second pulse of the pulsed waveform is applied to electrode_2 with changed polarity, and so on. As can be observed, pulse 6 and pulse 7 are applied to electrode_2 and electrode_3 simultaneously (and in this example, with changed polarity). In sum, FIG. 5 shows how stimuli are generated and distributed, thus controlling the delivery profile.

The optical sensing system 3, 12 is configured to measure and determine a relative change in the amount or concentration of the active agent contained in the hydrogel reservoir 9. The optical sensing system may comprise at least one light emitting means 3, such as a light emitting diode (LED) and at least one light detecting means 12, such as a photodiode. In FIGS. 2A and 2B, a light emitting means 3 and a light detecting means 12 are shown. One skilled in the art will understand that the optical sensing system may comprise other non-shown components, such as electronic components. The optical properties of the hydrogel change as the active agent is being delivered by the iontophoretic patch 20 to the skin/body. The optical sensing system measures optical properties of the hydrogel (mixed with active agent) comprised in the hydrogel reservoir 9 and compares the measured values with calibration values. There may be at least one optical sensing system per hydrogel reservoir comprising active agent. In the embodiment shown in FIGS. 2A and 2B, three independent hydrogel reservoirs have been depicted, each of them being associated to a different electrode (three concentric electrodes). Although for illustrative purposes only one optical sensing system 3, 12 has been depicted, in this case in the hydrogel reservoir associated to the most inner electrode, there may be at least one optical sensing system 3, 12 per hydrogel reservoir. Calibration values are experimental values previously obtained using the same hydrogel with a full range of concentrations of the active agent, and/or using numerical simulations, that is to say, according to a standard calibration procedure. For each hydrogel reservoir and active agent combination, a set of calibration values is obtained. Once the information from such calibration process is compared with the output of the optical sensing system 3, 12 at any moment of the delivery process, the feedback unit 1 sends the estimated current active agent release profile to control unit 11, which adjusts the stimulation pattern (stimulation parameters and selection of electrodes) in order to control the amount of the drug delivered to the skin. In other words, the stimulation pattern is defined by all electrical parameters defining pulse stimuli (amplitude, duration, frequency) and the location of delivery that is an address of the electrode used to deliver the stimuli. The optical sensing system 3, 12 is able to determine the concentration of the active substance contained in one or multiple hydrogel reservoirs 9 and to estimate the amount delivered at certain time instant to certain area of the skin. Based on the estimated amount of active substance delivered to the skin at a certain time, the time and space delivery profile are controlled.

The optical sensing system 3, 12 may be configured to measure changes of the transmission/absorption properties of the hydrogel reservoir containing an active agent (that is to say, the properties of the mixture or suspension of hydrogel and active agent), due to the fact that the transmission/absorption properties of the mixture vary as the active agent is delivered into the skin 24. This measurement of transmission/absorption properties may be done by the at least one light emitting means 3 and the at least one light detecting means 12. The determined absorption pattern (or determined transmission pattern) is compared with a reference pattern comprising experimental results obtained as a result of analyzing different concentrations of active agent mixed with hydrogel, in order to obtain the current concentration of the active substance in the hydrogel. The estimation of the amount of the drug delivered to the skin is done by calculating the difference between the amount of the drug initially introduced to hydrogel and the current concentration determined by the optical sensing system at any time instant during the delivery process. In other words, the relative difference in light absorption/transmission is measured; this relative difference correlates with the change of concentration of active agent in the reservoir.

The optical sensing system 3, 12 may be alternatively configured to measure changes in other optical properties of the mixture of hydrogel and/or active agent, such as changes in the refractive index or changes in fluorescence. Needless to say, changes in fluorescence may be measured provided the active substance is fluorescent at the wavelength of operation.

In order to achieve optical detection, the mixture of hydrogel and active agent comprised in said hydrogel reservoir 9 must be substantially translucent at the wavelength range of operation, in such a way that light at the operation wavelength manages to travel through the mixture. In other words, said mixture must be transparent or translucent or must have an absorbance value at the wavelength range of operation below a certain threshold enabling optical detection. Thus, an optically transparent or translucent hydrogel is preferably used.

The optical property to be measured will depend on the hydrogel reservoir/active agent combination. The wavelength range of operation, as well as the amount and type of light emitting means and light detecting means, may also be selected depending on such combination of hydrogel/active agent.

Figure 6:
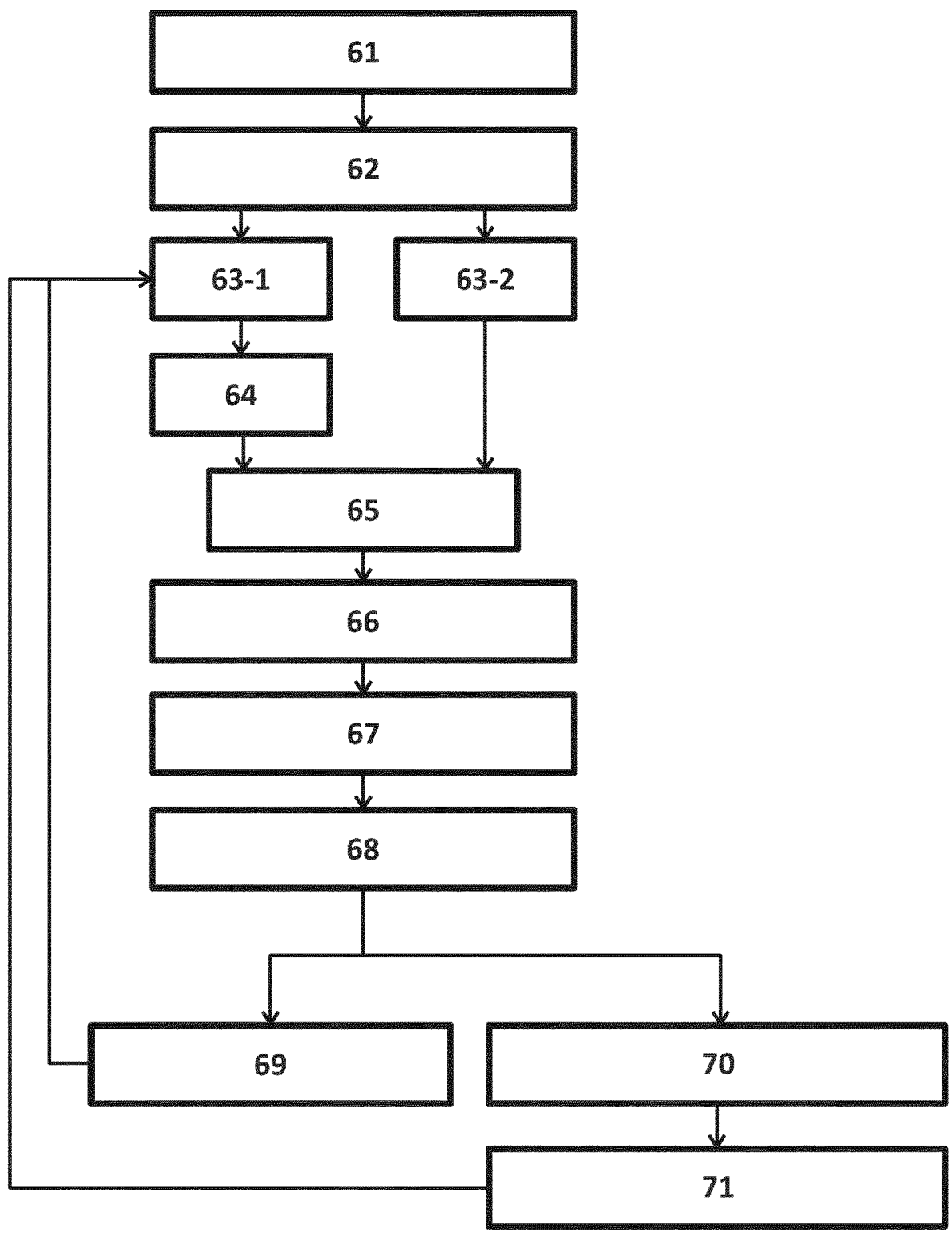
FIG. 6 depicts a flow diagram of an exemplary control loop implemented by the patch as schematically represented in FIG. 4.

FIG. 6 depicts a flow diagram of the control loop implemented by the electronic discharge means 40 embodied in FIG. 4. Once the device 20 is switched on (step 61), the electronic discharge means 40 enters into active mode and starts operation delivering drug at a predefined profile (step 62), such as a profile defined according to medical prescription. The control unit 11 generates stimulation parameters (step 63-1) that correspond to the predefined active agent delivery profile. The stimulation parameters may be initially generated at constant rate. The parameters are for instance: DC, AC or pulsed stimuli (mono-phase, bi-phase, bi-phase compensated or any other conventional pulsed stimuli), stimulation amplitude, frequency and duration. These parameters are sent to the stimulation unit 6. Substantially in parallel, the control unit 11 also generates (step 63-2) a stimulation location pattern corresponding to the electrode or electrodes to be stimulated, as well as the polarity of the electrodes to be stimulated with each pulse. The stimulation location pattern is delivered to the demultiplexing unit 10. Then, the stimulation unit 6 generates (step 64) stimulation pulses (pulsed waveform) from the instructions received from the control unit 11. This generated stimulation pulses are sent to the multiplexing unit 6. Then, the demultiplexing unit 6 transforms (step 65) the received input pulses (at step 64) into independent different signals for at least one electrode according to the location pattern (at step 63-2) and, at each time instant, each pulse generated by the stimulation unit 6 is delivered by the demultiplexing unit 6 to one or more of the electrodes 8 forming the electrode array, which are attached to the hydrogel reservoir 9, as explained with reference to FIG. 4. This way, in step 65 the electrical fields are created and the drug molecules (active agent) comprised in the hydrogel reservoir 9 are transferred from the reservoir 9 to the body and transported within the body according to the electrical field created.

Besides, when the electronic discharge means 40 enters into active mode, the control unit 11 also activates the feedback unit 1 to start operation. The feedback unit 1 activates the optical sensing system 3, 12. The optical sensing system 3, 12 starts measuring the drug concentration in the hydrogel reservoir 9 and provides a signal relative to this measurement to the feedback unit 1. At the start of operation, the optical sensing system 3, 12 measures the initial concentration of active agent in the reservoir 9 (or in each reservoir, assuming in general that there is more than one, for example one per electrode). The control unit 11 registers the initial concentration of active substance in the reservoir 9, for example in an internal memory. Calibration data for a plurality of hydrogel reservoir/active agent combination are also stored in memory means in control unit 11. Based on the stored calibration information, the light signal measured by the optical sensing means is transferred to a concentration value throughout the delivery session performed by the patch. The feedback unit 1 determines (step 66) this way the concentration in that moment of the active substance in the reservoir 9. Then, concentration information is transmitted to the control unit 11. From the instant concentration (concentration at that moment) in the reservoir 9 obtained from the feedback unit 1, the control unit 11 is able to determine (step 67) the real amount of active substance delivered to the body by subtraction of the initial concentration that is stored for example in an internal memory. The control unit 11 then compares (step 68) the real amount of delivered active substance with the theoretical amount that should have been delivered according to the predefined profile. If the real delivery profile is equal to the predefined profile (step 69) the control unit 11 continues to generate stimulation parameters as done in previous steps 63-1, 63-2. If the real delivery profile (as measured by the optical sensing system 3, 12) is NOT equal to the predefined profile (step 70), then the control unit 11 modifies the stimulation parameters and/or stimulation location pattern to achieve the desired delivering profile (step 71). The control unit 11 continues to generate stimulation parameters according to the updated profile and send corresponding instructions to the stimulation unit 6 (step 63-1) and to the demultiplexing unit 10 (step 63-2). In other words, the control unit 11 generates the new stimulation parameters and continues the control loop steps.

FIGS. 3A to 3C show possible embodiments of the electrodes design/configuration of the iontophoretic patch. These embodiments are not limiting. On the contrary, many alternatives can be embodied within the disclosure of the disclosure. FIG. 3A shows a concentric multi ring electrode system 441 according to a possible embodiment of the disclosure. The electrode system 441 comprises six concentric electrodes 441A 441B 441C 441D 441E 441F. It must be noted that although in this design the six electrodes are concentric, they may adopt any other disposition. In this embodiment, they are made of Ag/AgCl. FIG. 3A also shows the electrical contacts 416 (5 in FIG. 2B) of the electrode substrate 417 (2 in FIG. 2B). The most inner electrode 441A may have a polarity which is opposite to the polarity of the remaining electrodes 441B 441C 441D 441E 441F. The remaining electrodes 441B 441C 441D 441E 441F can have equal or unequal electric potential. It is remarked that unequal electric potential contributes to the spatial distribution of the substance. This is explained next, in relation to FIGS. 7A to 7J. The internal electrode 441A may have positive polarity (anode) and all the external electrodes 441B 441C 441D 441E 441F may have negative polarity (cathode or indifferent electrode). This means that when the electrodes are activated through the electronic discharging means of the patch, the evolution of the transdermal delivery of the substance—when there is one—is controlled both temporally and spatially.

When a current/voltage is applied, the spatial control of the transdermal delivery of the substance is achieved thanks to the different surrounding electrodes: the closer to the most inner electrode 441A an electrode is, the less deep within the skin the substance travels. On the contrary, the most external electrode 441F applies less attraction of the electric field, as a consequence of which the substance travels deeper within the skin rather than travelling parallel to the skin surface.

FIG. 3B shows another concentric electrode system 443 (front view on the left and rear view on the right). The electrode system 443 comprises two concentric electrodes 443A 443B. In this embodiment, they are made of Ag/AgCl. The electrical contacts 416 (5 in FIG. 2B) of the electrode substrate 417 (2 in FIG. 2B) are also shown. In this embodiment, the most inner electrode 443A has round shape, but can alternatively have any other shape. The outer electrode 443B totally surrounds the first one 442A. Variation in relative size and distance between electrode segments will define the shape of electric field underneath the electrode. Generally speaking, and not taking into account dielectric inhomogeneity of the skin, a larger distance between the electrodes results in "deeper" electric fields of biologically significant magnitude and, consequently, deeper penetration of a target active agent. Moreover, assuming that an active substance is to be delivered under the central electrode, the increased size of the central electrode can accommodate a larger substance-loaded matrix and thus enables to increase the overall quantity of the drug that is to be delivered.

FIG. 3C shows a matrix electrode 444. In this embodiment, a single electrode substrate 417 (2 in FIG. 2B) has a plurality of electrode systems. In this particular example, there are 3×4 electrode systems. Each electrode system can have any particular configuration, like the ones described in FIGS. 3A and 3B or any other configuration. In the example of FIG. 3C, there are 12 electrode systems, each of them comprising two concentric electrodes, for example made of Ag/AgCl. This implementation is especially useful in certain applications, for example for the simultaneous delivery of multiple controlled amounts of allergen substances (probes) from a patch to the skin (generally but not limited onto the forearm) to perform an allergy test. Each electrode set or electrode array can be designed for the transdermal delivery of a different substance. In other words, each of the 3×4 two electrode segments is used as a single allergen probe. Depending on the substance, the electrode array may have a specific configuration (number of electrodes, width of the strip which forms the electrode (for example, ring), separation between consecutive electrodes, and so on). The allergen substance is loaded in the hydrogel reservoir 9 under the central electrode and the concentric surrounding electrode is used as ground electrode (it is not loaded with allergen substance). One or more electrode sets in the array can be used as "blanks" or controls and in that case no allergen substance is loaded in any of the two segments. This embodiment uses similar electronic circuitry, power supply means and output stage to previous embodiments. Spatial control of allergen delivery is predefined by the design of the two segment element while the temporal delivery control can be changed in real time through stimulation parameters defined independently for each of the two electrode segments, by the control unit 11.

FIGS. 7A to 7J show a simulation model of the behavior of the electric field and ionic current flow as it penetrates a user's skin, in a patch having concentric electrodes, such as the one shown in FIG. 3A, and having a cross-section like the one illustrated in FIG. 2A, when a current/voltage is applied to the electrodes of the patch. The substance penetrates within the skin. The penetration and spatial distribution of the substance within the skin can be controlled by adjusting the distribution of the electric field generated by the electrodes, which can be achieved through the electrode layout and the spatio-temporal pattern of activation of the electrodes. The figures show the time evolution of delivery by a two-electrode system, where polarity is changed.

In FIGS. 7A to 7J, for the sake of simplicity, the electric field distribution and consequent current density is simulated for three concentric electrode segments (one central 441A and two surrounding electrodes 441B 441C) and in three different applied electric potential scenarios.

Figure 7A:
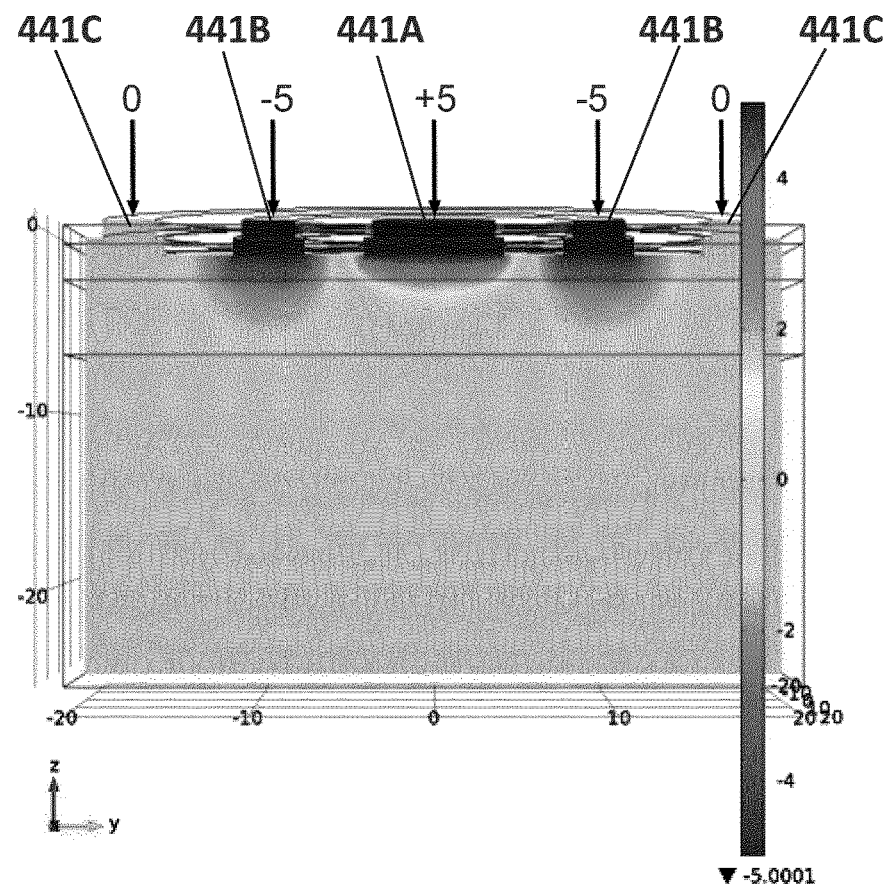
FIGS. 7A to 7L show a simulation of the electric field and current flow and consequent spatio/temporal drug delivery profile in a user's skin delivered by the patch of the disclosure.
Figure 7B:
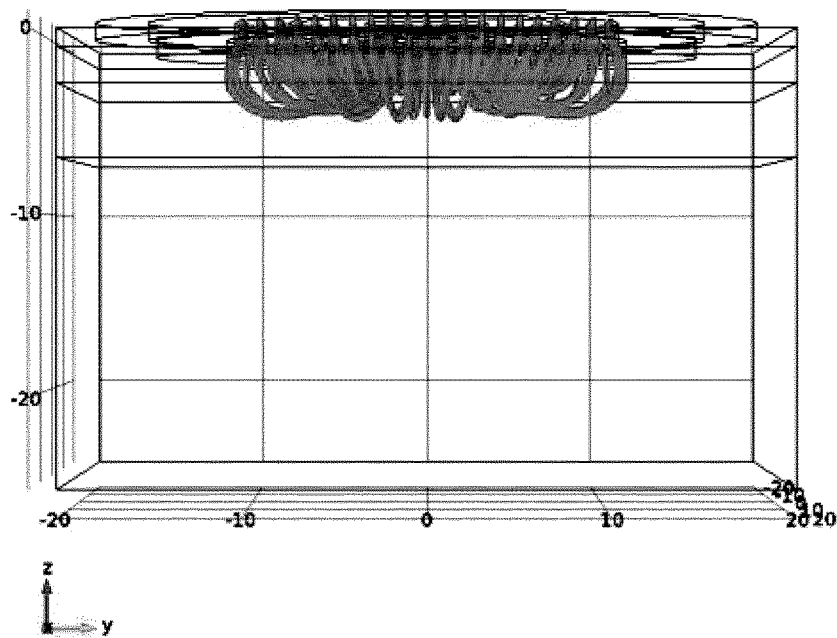

In FIG. 7A, the electric potential difference between the central electrode 441A and the first surrounding ring electrode 441B is 10V, while the electric potential difference between the central electrode 441A and the second ring electrode 441C is 5V. Consequently, the current density profile shown in FIG. 7B corresponding to the electric field distribution of FIG. 7A, shows a confined skin element (area, volume) where the ionic current induced by the electric field profile contributes to the substance/active agent penetration. The delivery profile is shallow and dense, confined only between electrodes 441A and 441B. It is notable that the electrode 441B with higher potential difference does not allow the current/substance to "escape" to the lower potential difference region between electrodes 441B and 441C. Indeed, if we consider a positively charged particle in the immediate vicinity of electrode 441A, it will be repelled from 441A and attracted to 441B as its trajectory is determined by the net potential difference between 441A and 441B that is 10V. Similarly, since the 441C has 0V potential, the potential difference with respect to 441B is −5V and no positively charged particle can move from the vicinity of 441B towards 441C, resulting in confinement of positively charged particles delivered from the vicinity of 441A inside the 441A-441B region.

Figure 7C:
Figure 7D:
Figure 7E:

FIGS. 7C to 7E show the time evolution (1200 seconds) of drug penetration profiles with the electrode configuration of FIG. 7A. FIG. 7C represents the start (0 seconds) of the penetration profile. FIG. 7D represents the penetration profile at 600 seconds. FIG. 7E represents the penetration profile at 1200 seconds. As can be observed, the drug is clearly delivered in shallow.

Figure 7F:
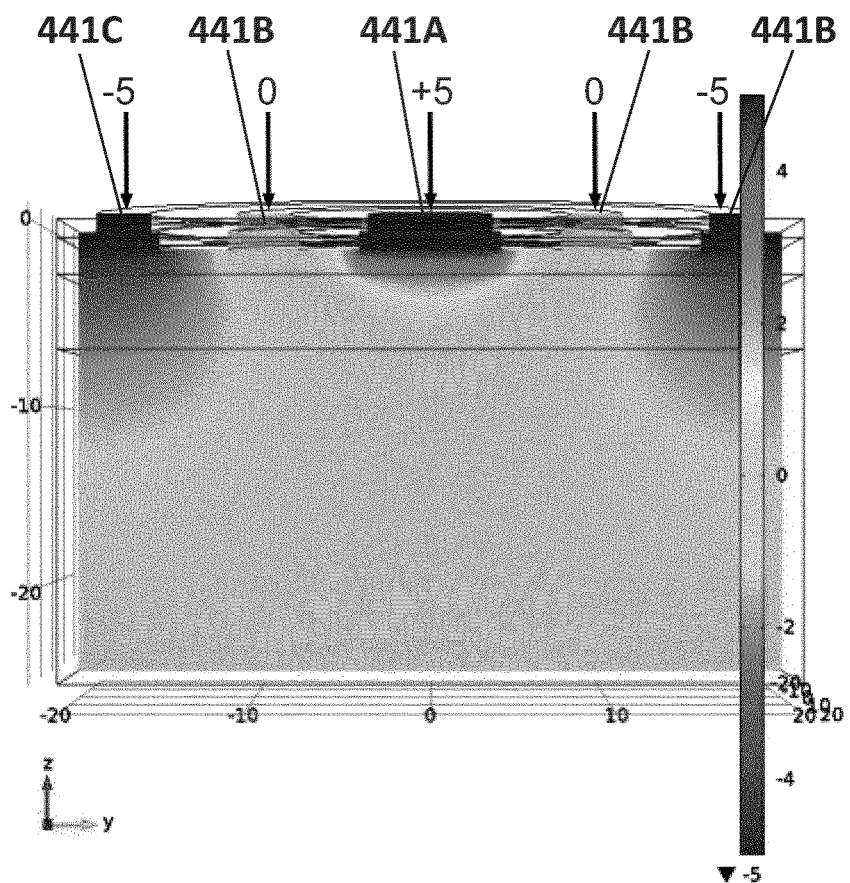

In FIG. 7F, the electric potential difference between the central electrode 441A and the first surrounding ring electrode 441B is 5V, while the electric potential difference between the central electrode 441A and the second ring electrode 441C is 10V. Consequently, the current density flow illustrated in FIG. 7G, corresponding to the electric field distribution of FIG. 7F, shows a confined skin element (area, volume) in which the ionic current induced by the electric field profile contributes to the substance/active agent penetration. The delivery profile is deeper than in FIG. 7B and less dense, confined between electrodes 441A and 441C. It is notable that the increase in separation/distance between electrode rings with higher potential difference increases the depth of the delivery profile and that some current still "sinks" in electrode 441B, with lower potential difference with respect to electrode 441A.

Figure 7G:
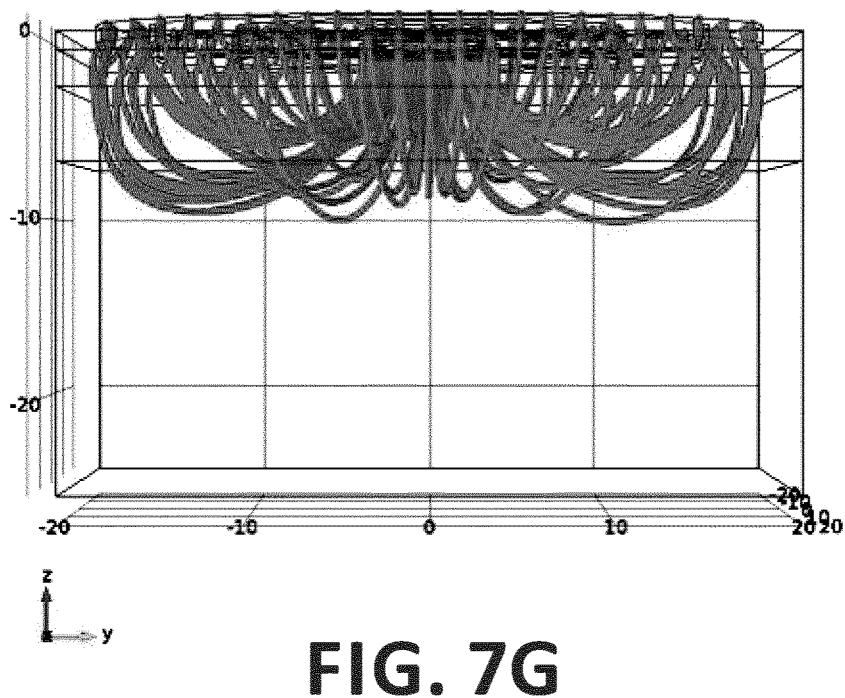
Figure 7H:
Figure 7I:
Figure 7J:

FIGS. 7H to 7J show the time evolution (1200 seconds) of drug penetration profiles with the electrode configuration of FIG. 7F. FIG. 7H represents the start (0 seconds) of the penetration profile. FIG. 7I represents the penetration profile at 600 seconds. FIG. 7J represents the penetration profile at 1200 seconds. As can be observed, the drug is clearly delivered in shallow. Comparing the profiles of FIGS. 7C-7E to the profiles of FIGS. 7H-7J, in FIGS. 7C-7E the drug is delivered in a much more confined skin volume, while in FIGS. 7H-7J it is delivered in a much deeper and larger volume.

Figure 7K:
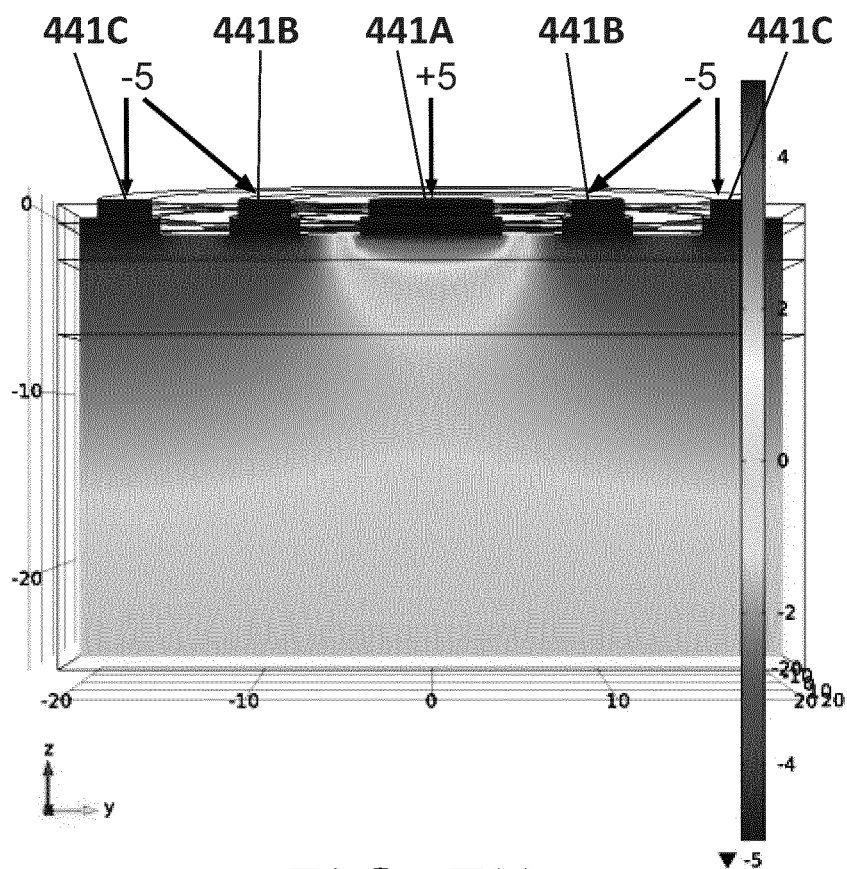
Figure 7L:
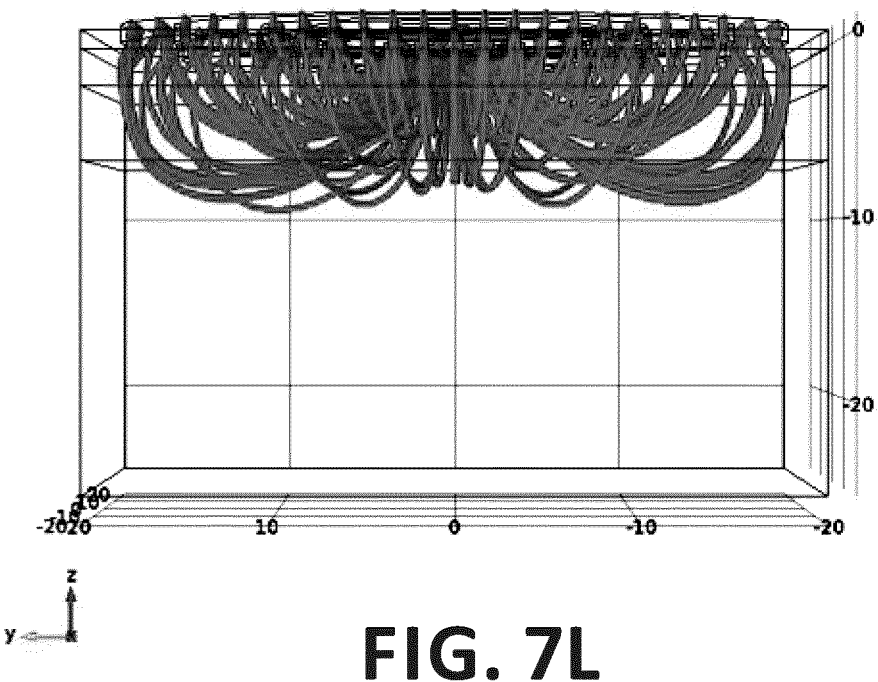

In FIG. 7K, the electric potential difference between the central electrode 441A and both surrounding electrodes 441B 441C is 10V. Consequently, the current density flow illustrated in FIG. 7L, corresponding to the electric field distribution of FIG. 7K, shows a confined skin element (area, volume) in which the ionic current induced by the electric field profile contributes to the substance/active agent penetration. The delivery profile (FIG. 7L) is deeper than in FIG. 7B and has higher density than in FIG. 7G, while still confined between electrodes 441A and 441C.

As apparent from the above described example, control of substance delivery in a confined space and time domain is possible when combining time dependent changes of the polarity and intensity, as well as other stimulation parameters, of the electric field applied to an electrode array. The substance to be delivered moves laterally from the central area to the first concentric electrode (FIG. 7B) and to the second concentric electrode (FIG. 7G). In this last case, the substance penetrates deeper in the tissue. The confinement of the substance/active agent in a spatial location (area/volume) is achieved with active control of transversal and lateral components of the applied electrical stimuli. This can be appreciated for example in FIGS. 7A and 7B, which show the current density vectors. Each vector has transversal and lateral projection. Hence, by controlling the electrode activation and potential delivered on each electrode, the transversal and lateral component/projections of the vectors are changed, thus changing the delivery profile. Since the location of the substance/active agent in the skin can be predicted, depending on the application, a patch can be designed to deliver the substance/active agent more or less deeper in the skin, or more or less spread within a predetermined depth, or whatever.

The parameters of the active agent penetration and spatial distribution within the skin are defined with the design of the electrodes, the distance between neighboring electrodes and the stimulation pattern. The electrode system enables independent activation of each of the electrodes. One or several electrodes can be synchronously or asynchronously activated. For each electrode, polarity, electric potential amplitude, frequency, duration and profile of voltage/current pulses and configuration of activated electrodes, among other parameters, can be changed independently by means of the microprocessor comprised in the control means. In other words, the control means is capable of programming different iontophoretic session protocols including variation of electrode configuration and stimulation parameters in order to adapt to the specific needs of every patient, treatment, dosage, drug/substance, drug carrier formulation and drug carrier matrix.

In sum, the described patch, in its different embodiments and implementations, provides spatial and temporal delivery control and release of active substances transdermally, in such a way that the three-dimensional distribution or confinement of one such target active substance inside the skin can be established, monitored and controlled in form of space and time defined delivery profile. This is achieved through real time optical detection of the drug concentration in the hydrogel, and through processing means comprised in control unit 11, wherein the current drug delivery profile is compared with a predefined delivery profile based on experiments and numerical simulations. The predefined stimulation pattern is adjusted based on an optical detection system feedback. In other words, the device permits the localized delivery of a substance/active agent in certain areas/volumes of the skin and underlying tissue muscles, nerves or bones according to controlled temporal delivery patterns.

This is achieved by controlling the shape of the electric field that is generated inside the skin for a given potential applied. This property can be used to achieve highly localized drug delivery, to generate concentration gradients of an active substance over a given skin surface, to control the depth of penetration of an active substance into the skin, etc. In other words, a substance (i.e. molecule) can be moved in any desired direction at any time instant during the iontophoretic session. For example, the device can be used for localized topical delivery of substances, such as cytostatic or anesthetic substances, that should not reach the vascularized part of the skin.

As apparent from the content of this description, the patch offers a solution to the problem of transdermal delivering a substance/active agent in a localized area/volume of the skin and underlying tissue. The patch controls effectively the real amount of drug that is delivered into the skin at any moment in order to deliver the drug according to a desired delivery profile. The control of the dosage is performed continuously, therefore the electrical stimuli are adjusted in real time to obtain the desired amount of active substance transferred to the body. The patch can be used in a therapeutic or non-therapeutic treatment based on transdermal delivery of biologically active agents by iontophoretic techniques. The patch can also be used for the simultaneous delivery of a plurality of allergen probes in a diagnostic method for diagnosing at least one allergy, the diagnostic method being based on transdermal delivery of biologically active substances by iontophoretic techniques.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the disclosure as defined in the claims.

The invention claimed is:

1. An iontophoretic patch for transdermal delivery of biologically active agents, comprising:
   a printed circuit board;
   at least two electrodes connected through electric contacts to said printed circuit board;
   at least two hydrogel reservoirs configured to, in use of the iontophoretic patch, be disposed on a user's skin, wherein at least one of said hydrogel reservoirs comprises at least one active agent carried therein to be delivered into the user's skin, wherein said at least two electrodes are in contact with respective at least two hydrogel reservoirs;
   a control unit embedded on the printed circuit board, the control unit being configured to generate a stimulation pattern comprising a plurality of stimulation parameters to be delivered to a plurality of stimuli locations on the skin, wherein said at least two electrodes are configured to be activated/deactivated following said stimulation pattern;
   a stimulation unit embedded on the printed circuit board, the stimulation unit being configured to generate a time sequence of pulses from said plurality of stimulation parameters generated by the control unit;
   a demultiplexing unit embedded on the printed circuit board, the demultiplexing unit being configured to, from the time sequence of pulses generated by said stimulation unit and from said stimuli locations generated by said control unit, perform independent spatio-temporal distribution of the electrical pulses comprised in said time sequence of pulses to at least one electrode of said at least two electrodes, wherein each of said at least two electrodes are connected through respective electric contacts to said demultiplexing unit, each electric contact being activated independently through the demultiplexing unit;
   at least one optical sensing system disposed in at least one of said hydrogel reservoirs, for, in use of the iontophoretic patch, continuously measuring an amount of said at least one active agent in said at least one hydrogel reservoir; and
   a feedback unit embedded on the printed circuit board, the feedback unit being configured to estimate, from said amounts of at least one active agent measured at said at least one optical sensing system, a temporal delivery profile of said at least one active agent into the skin,
   said control unit being further configured to compare an estimated delivery profile provided by the feedback unit with a desired delivery profile and to continuously modify said generated stimulation pattern by changing at least one of said plurality of stimulation parameters to be provided to the stimulation unit and/or said stimuli locations to be provided to said demultiplexing unit.

2. The iontophoretic patch of claim 1, wherein said at least two electrodes are concentric, and said at least two hydrogel reservoirs with which said at least two electrodes are in contact, are also concentric.

3. The iontophoretic patch of claim 1, wherein said at least one optical sensing system comprises at least one light emitting means and at least one light detecting means.

4. The iontophoretic patch of claim 1, wherein said control unit is configured to control one or more of the following parameters of a stimulation pattern:
   polarity, amplitude, frequency of voltage/current pulses, duration of voltage/current pulses and activation of at least one electrode from the at least two electrodes.

5. The iontophoretic patch of claim 1, wherein the at least one hydrogel reservoir comprises a mixture of hydrogel and active agent, wherein the mixture of hydrogel and active agent comprised in said at least one hydrogel reservoir is translucent at the wavelength range of operation, thus enabling optical detection by said at least one optical sensing system.

6. The iontophoretic patch of claim 1, wherein the at least one hydrogel reservoir comprises a mixture of hydrogel and active agent, wherein the hydrogel comprised in said at least one hydrogel reservoir is configured to provide a tunable concentration gradient profile of active agent and tunable electrical conductivity, thus controlling concentration and electrical conductivity within the at least one hydrogel reservoir.

7. The iontophoretic patch of claim 1, wherein each electrode of said at least two electrodes comprises electrical contacts independent from electrical contacts of other electrodes of said at least two electrodes, thus enabling independent delivery of electrical stimuli.

8. The iontophoretic patch of claim 1, further comprising power supply means.

9. The iontophoretic patch of claim 1, wherein said at least one biologically active agent to be delivered in the skin is one of the following list: a drug, a prodrug, a tissue growth factor or a biomedical probe, said substance being in the form of a compound, protein, peptide, nucleotide, ribozyme, dsRNA, RNAi, vaccine or a combination thereof.

10. Use of the iontophoretic patch of claim 1, in a treatment based on transdermal delivery of biologically active agents by iontophoretic techniques.

11. The use of the iontophoretic patch of claim 1, for the simultaneous delivery of a plurality of allergen probes in a method for diagnosing at least one allergy, the diagnostic method being based on transdermal delivery of biologically active substances by iontophoretic techniques.

12. A method of controlling the delivery of at least one active agent from an iontophoretic patch, the method including the following steps:
   delivering at least one active agent according to an initial profile by applying a stimulation pattern to at least two electrodes in contact with respective at least two hydrogel reservoirs, in contact with a user's skin, wherein at least one of said hydrogel reservoirs comprises said active agent, wherein said stimulation pattern comprises a plurality of stimulation parameters and electrical stimuli location,
   estimating the amount of said at least one active agent within said at least one hydrogel reservoir by measuring an optical parameter in said hydrogel reservoir,
   determining the delivery profile of active agent being delivered to the skin by comparing the amount of delivered active agent with the amount thereof corresponding to said initial profile,
   when the determined delivery profile does not match the initial profile, modifying the stimulation parameters and/or stimulation location pattern to achieve the initial delivering profile.

13. The iontophoretic patch of claim 1, wherein the control unit, the stimulation unit, the demultiplexing unit and the feedback unit are comprised in a single chip embedded on the printed circuit board.

14. The iontophoretic patch of claim 1, wherein the control unit, the stimulation unit, the demultiplexing unit and the feedback unit are each implemented in a different chip embedded on the printed circuit board.

15. The iontophoretic patch of claim 1, wherein the control unit, the stimulation unit, the demultiplexing unit and the feedback unit are implemented in several chips embedded on the printed circuit board.

16. The iontophoretic patch of claim 1, wherein the at least one optical sensing system is configured to measure the amount of said at least one active agent in said at least one hydrogel reservoir at a sampling frequency comprised with the following range: from 0.1 to 100 Hz.

17. The iontophoretic patch of claim 1, wherein the feedback unit is configured to estimate the temporal delivery profile of said at least one active agent into the skin, by translating a light signal measured by the optical sensing means into a concentration value.

* * * * *